United States Patent
Duggal et al.

(10) Patent No.: US 12,314,688 B2
(45) Date of Patent: May 27, 2025

(54) INTEGRATED APPLICATION DEVELOPMENT SYSTEMS AND METHODS

(71) Applicant: Engineer.ai Global Limited, London (GB)

(72) Inventors: Sachin Dev Duggal, London (GB); Rohan Patel, London (GB); Priyanka Kochhar, London (GB)

(*) Notice: Subject to any disclaimer, the term of this patent is extended or adjusted under 35 U.S.C. 154(b) by 293 days.

(21) Appl. No.: 17/903,166

(22) Filed: Sep. 6, 2022

(65) Prior Publication Data

US 2023/0083894 A1    Mar. 16, 2023

Related U.S. Application Data

(63) Continuation-in-part of application No. 17/120,118, filed on Dec. 12, 2020, now Pat. No. 11,720,330,
(Continued)

(51) Int. Cl.
*G06F 8/30* (2018.01)
*A61M 21/02* (2006.01)
(Continued)

(52) U.S. Cl.
CPC ............ *G06F 8/316* (2013.01); *A61M 21/02* (2013.01); *G06F 8/20* (2013.01); *G06F 8/36* (2013.01);
(Continued)

(58) Field of Classification Search
CPC .. A61M 2021/0016; A61M 2021/0022; A61M 21/02; G06F 8/20; G06F 8/316;
(Continued)

(56) References Cited

U.S. PATENT DOCUMENTS 6,016,394 A    1/2000   Walker
6,697,824 B1   2/2004   Bowman-Amuah
(Continued)

FOREIGN PATENT DOCUMENTS

CN    102880455 A    1/2013
CN    107346249 A    11/2017
(Continued)

OTHER PUBLICATIONS

International Preliminary Report on Patentability and Written Opinion for International Patent Application No. PCT/ EP2020/085866, issued May 17, 2022, 9 pages.
(Continued)

*Primary Examiner* — Ted T. Vo
(74) *Attorney, Agent, or Firm* — Fox Rothschild LLP

(57) ABSTRACT

A system for developing software provides automatically identifies, based on wireframe images, features from a library of features for a custom software application, implements simulations of a plurality of the features available for demonstration through the graphical user interface, stores blocks of source code for each feature in a source code repository wherein the blocks are adapted to provide an actual application when compiled by developers, receives from the client device, by a server running a software building component, one or more selected features for the software application, automatically integrates, by the software building component, the one or more selected features to generate an integrated feature set based on attributes of each of the selected features and an inter-feature rules set, and generates an interactive visualization of a navigable prototype of the software application based on the integrated feature set.

20 Claims, 13 Drawing Sheets

Related U.S. Application Data which is a continuation-in-part of application No. 16/854,805, filed on Apr. 21, 2020, now Pat. No. 11,086,599, which is a continuation of application No. 15/786,431, filed on Oct. 17, 2017, now Pat. No. 10,649,741.

(60) Provisional application No. 62/948,100, filed on Dec. 13, 2019, provisional application No. 62/408,935, filed on Oct. 17, 2016.

(51) Int. Cl.
| | | |
|---|---|---|
| *G06F 8/20* | (2018.01) | |
| *G06F 8/36* | (2018.01) | |
| *G06F 8/71* | (2018.01) | |
| *G06Q 10/0631* | (2023.01) | |
| *G06Q 30/0283* | (2023.01) | |
| *A61M 21/00* | (2006.01) | |

(52) U.S. Cl.
CPC .......... *G06F 8/71* (2013.01); *G06Q 10/06311* (2013.01); *G06Q 30/0283* (2013.01); *A61M 2021/0016* (2013.01); *A61M 2021/0022* (2013.01)

(58) Field of Classification Search
CPC ....... G06F 8/36; G06F 8/71; G06Q 10/06311; G06Q 30/0283
USPC ................................................. 717/101–109
See application file for complete search history.

(56) References Cited

U.S. PATENT DOCUMENTS

| | | | |
|---|---|---|---|
| 7,783,523 B2 | 8/2010 | Lopez et al. | |
| 8,413,062 B1 | 4/2013 | Little | |
| 8,458,009 B1 | 6/2013 | Southworth | |
| 8,621,423 B2 | 12/2013 | Knight et al. | |
| 8,640,027 B2 | 1/2014 | Chandhoke et al. | |
| 8,997,038 B2 | 3/2015 | Bozek et al. | |
| 9,268,544 B2 | 2/2016 | Kang et al. | |
| 9,286,040 B2 | 3/2016 | Halley et al. | |
| 10,223,654 B2 * | 3/2019 | Dhiman | G06Q 10/063118 |
| 10,296,308 B2 | 5/2019 | Lance | |
| 10,469,741 B2 | 11/2019 | Ishibashi | |
| 10,521,199 B2 | 12/2019 | Ganesan et al. | |
| 10,540,153 B2 | 1/2020 | Stachura | |
| 11,061,650 B2 * | 7/2021 | Turek | G06F 40/00 |
| 11,221,833 B1 * | 1/2022 | Huang | G06F 9/451 |
| 2003/0018952 A1 | 1/2003 | Roetzheim | |
| 2005/0066304 A1 | 3/2005 | Tattrie et al. | |
| 2006/0259442 A1 | 11/2006 | Iqbal | |
| 2008/0235155 A1 | 9/2008 | Thywissen | |
| 2009/0037287 A1 | 2/2009 | Baitalmal et al. | |
| 2011/0088011 A1 | 4/2011 | Ouali | |
| 2011/0271246 A1 | 11/2011 | Fujihara | |
| 2011/0276354 A1 | 11/2011 | Bijani et al. | |
| 2012/0331439 A1 | 12/2012 | Zimmermann et al. | |
| 2014/0173454 A1 | 6/2014 | Sanchez | |
| 2016/0055079 A1 | 2/2016 | Hanna | |
| 2016/0092179 A1 | 3/2016 | Straub | |
| 2016/0139888 A1 | 5/2016 | Iyer et al. | |
| 2018/0107459 A1 * | 4/2018 | Duggal | G06F 8/20 |
| 2020/0285450 A1 | 9/2020 | Das et al. | |
| 2021/0390032 A1 | 12/2021 | Quaglio et al. | |

FOREIGN PATENT DOCUMENTS

| | | |
|---|---|---|
| CN | 110457031 A | 11/2019 |
| CN | 110515614 A | 11/2019 |
| CN | 111158670 A | 5/2020 |
| JP | 2013-25612 | 2/2013 |
| KR | 101975272 B1 | 5/2019 |
| WO | 2015/136607 A1 | 9/2015 |
| WO | 2021116471 | 6/2021 |

OTHER PUBLICATIONS

International Search Report and Written Opinion for International Patent Application No. PCT/EP2020/085866, mailed Mar. 31, 2021 (11 pages).

Notification of Transmittal of the International Search Report and the Written Opinion of International Searching Authority, or the Declaration for International Application No. PCT/US2017/057030, International Filing Date Oct. 17, 2017, mailed Jan. 4, 2018, 7 pages.

Aminullah, Sharlene, "Cost Estimation of Service Delivery in Cloud Computing", Aug. 2012, Arjuna Technologies Ltd., 95 pages (2012).

Curtis, Nathan, "Modular Web Design—Creating Reusable Components for User Experience Design", 2010, Peachpit Press, 328 pages (2010).

Puerta, Angel, et al., "The UI Pilot: A Model-Based Tool to Guide Early Interface Design", ACM, pp. 215-222 (2005).

Chen et al., "Wireframe-Based UI Design Search Through Image Autoencoder," Retrieved from the Internet: <https://arxiv.org/pdf/2103.07085vl.pdf>ACM Trans. Softw. Eng. Methodol., vol. 29, No. 3, Article 19, 31 pages (May 2020).

* cited by examiner

WIREFRAME OF A SCREEN

SOFTWARE APPLICATION SCREEN

INTEGRATED APPLICATION DEVELOPMENT SYSTEMS AND METHODS

CROSS REFERENCE TO RELATED APPLICATIONS

This application is a continuation-in part application of and claims the benefit of U.S. patent application Ser. No. 17/120,118, filed Dec. 12, 2020, which claims priority to 62/948,100 and U.S. patent application Ser. No. 17/349,807, filed Jun. 16, 2021, which claims priority to 63/039,064, filed Jun. 15, 2020. The application claims priority to each and incorporate each by reference in their entirety.

FIELD OF THE INVENTION

Embodiments of the present invention related to the field of software development. Specifically, embodiments of the present invention are related to systems and methods for developing software involving automated feature identification and instant prototyping.

BACKGROUND

The process of working with vendors to develop desired software from initial idea through final software involves many stages and can take many months or years from start to finish. This process can oftentimes result in projects dying because of the complexity and the extended time from the initial excitement of the new idea to receiving anything tangible while also paying for potentially increasing development costs. Techniques for improving this process, which can improve the design process and provide greater efficiencies for vendors, are desired.

As generally understood, the conventional approach for developing a custom software application is to engage designers to develop the interface designs and the visual component, and software developers to implement the customer requirements for the software application, including the design aspect into working source and object code (e.g., adapted for selected operating systems). The interactions with the software developer may involve initial conversations, artwork, or input from designers (that develop the user interface layout). The three-party interaction can result in deficiencies in efficiency, pricing, and consistency. User Interface (UI) layout and functionality is an important aspect of software development. The software development process can include a step in which one or more display screens are generated on a device to provide a graphical visual interface. These are generated using executable code to provide the front end (whether static or dynamic). The visual elements of the display screen generated by the software executable can be graphical elements generated, for example, by a software module. The visual elements can be images that are retrieved for an image file. Other visual elements can be fonts, colors, icons, menu structures, buttons, etc. The software development process is, in a standard way for development, structured where a designer generates visual images (e.g., static images) such as in an image file as the visual design that the executable software is to deliver when the software is developed and running. A good UI facilitates the use and enjoyment of an application and can be dispositive of its success. Significant resources are poured into optimal UI design that effectively combine aesthetics and functionality. The process involves original designs (i.e., what the designer and the customer agreed on) and the respective UIs (i.e., what the developer implemented in the front-end and ultimately appears on the screen of a computing device).

There can be one or more technical problems related to software development and the integration of source code development and user interface design for software applications.

SUMMARY OF THE INVENTION

According to embodiments of the present invention, a system for creating software is disclosed. The system can be an online software development system for developing software applications. Online can refer to the use of an Internet connection to be able to use the system. The system comprising at least one processor; and at least one memory operatively coupled to the at least one processor, the at least one processor configured to acquire computer readable instructions stored in the at least one memory and execute the instructions comprising instructions to cause the system to: receive a plurality of wireframes prepared for a proposed custom software application sought to be developed by a user of the online software development system; perform a comparison between the wireframes and software screens for previously developed custom software applications; detect matches between the wireframes and software screens; identify features available on the online software development application for developing custom software applications that correspond to the matches; provide a graphical user interface on a display of a client device, and implement simulations of a plurality of features available for demonstration through the graphical user interface; store blocks of source code for each feature in a source code repository, wherein the blocks are adapted to provide an actual application when compiled by developers; receive from the client device, by a server running a software building component of a software development application, one or more selected features for the proposed custom software application; automatically integrate, by the software building component, the one or more selected features to generate an integrated feature set based on attributes of each of the selected features and an inter-feature rules set, and generate on the graphical user interface an interactive visualization of a navigable prototype of the software application based on the integrated feature set.

The system can include computer readable instructions that cause the processor to generate a specification that identifies components of software to be developed to complete the proposed custom software application.

The system can be configured wherein the comparison comprises comparison of images of wireframes with images of software screens previously developed for available features on the online software development system.

The system can comprise a plurality of use-selectable features that are automatically detected from the wireframes to be included in the proposed customer software application.

The system can be configured wherein the instructions further comprise instructions to cause the processor to provide a normalization engine that operates on the wireframes.

The system can be configured wherein the instructions further comprise instructions to cause the processor to generate images of developed software screens and store an association of the images to corresponding features.

The system can be configured wherein the instructions further comprise instructions to provide a normalization engine that operates on the generated images of developed software screens.

The system can be configured wherein the instructions further comprise instructions to cause the process to generate digital rules or parameters that translate image content of wireframe screens to available features on the software development system.

BRIEF DESCRIPTION OF THE DRAWINGS

Various features of examples and embodiments in accordance with the principles described herein may be more readily understood with reference to the following detailed description taken in conjunction with the accompanying drawings, where like reference numerals designate like structural elements, and in which.

Figure 1:
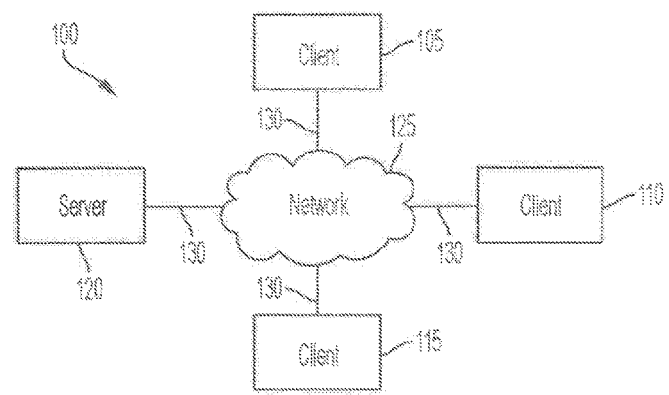
FIG. 1 is a simplified block diagram of a distributed computer network according to an embodiment of the present invention.

These and other features are detailed below with reference to the above-referenced figures.

DETAILED DESCRIPTION OF THE INVENTION

Embodiments of the present invention provide for a software development application that receives and loads an image that is a designer's illustration of a display screen (or a portion thereof), which may have been entirely or partially manually prepared by an illustrator on an illustration software application, and detects one or more features of the software application under development by analyzing the illustrations. Based on the detected features, the software development application can generate a rapid prototype of the desired software application based on an underlying prototype architecture.

The software development application applies an algorithm in which the software development application traverses the contents of the image of the designer illustration image. The traversal can be sequential, simultaneously, or some combination thereof. One or more algorithms can be applied as part of the traversal that identifies correspondence between the illustration and software features. One or more algorithms can be applied that generate a prototype from the identified features.

The system can automatically by way of a data channel, API, or upload of files receive wireframe designed for a new customer application of the customer and convert that conceptual rendering to a set of concrete features (automatically identified by the system using the wireframes from a library of features) that are then integrated by the system to generate a live initial prototype in the sense of a visually playable set of screens (e.g., a browser simulation). The prototype is preferably not at the level of an application that would be installed on a mobile device or computer as an initial working version. This provides rapid development and engagement in the process and specificity for the development process.

Embodiments of the present invention disclose a system and method that automate aspects of developing software applications. Specifically, embodiments of the present invention provide a process as part of a customer driven application development platform that includes a process stage that generates an early prototype of the customer's desired application for inspection and fine tuning by the customer. The platform can generate the early prototype by receiving wireframes and automatically detecting which features are found in the proposed custom software application. A computer-implemented process can be implemented that provides a platform that is accessible by a customer using conventional browsers. The platform can be a cloud service that permits the user to interact with the platform through graphical user interfaces to complete the different stages of the application development process. That would generally be understood to involve a combination of one or more computers, software implemented on one or more computers that configures the computers to provide a specialized application, and online, Internet website access to the functionality through a (conventional) browser or in some cases, a software application (e.g., a mobile app).

The platform or system can be structured to define features as individual elements having certain characteristics such as meta data. The primary focus of this application is a subsystem directed to generating detecting features from wireframes and in response to the detected features, generating an instant prototype or quick delivery prototype. The sub-system may be part of a platform or system configured to generate code for a software application based on selected features and on the instant prototype. The customer can interact with the platform and by as little as providing wireframes be able to view and interact with a visual prototype. This is performed by providing a visual representation of the screen that will be displayed by the desired software based on the selected features. The prototype will be functional in that, at the minimum, there will be live areas in displayed screens (e.g., a representation of a mobile phone screen displayed through a web browser or other graphical user interface) that the customer can "click" or interact with that, in response, will display a connected next screen. The platform can permit the user to edit the prototype or prototype demonstration by changing the flow of the screen using interactive visual options, such as through a displayed screen on a browser.

The system can include a wireframe tool, including a graphical user interface that is configured to allow a user to illustrate the software screens of the user's proposed software application. This can involve menu options such as window frames, buttons, or other visual illustrations of desired software display screens of the application. The system can be configured to receive images, pictures, or scans of wireframes. For example, a user can hand-draw wireframes and use photographs or scans of the drawings as an input to the system for the feature detection process. Or, for example, there may be a third-party wireframe software tool that is preferred and the user can generate images of PDFs of the wireframes from that software tool and provide the images or PDFs as input to the system for the feature detection process. In some embodiments, the system can be configured to include an application program interface or automated data channel that feeds the wireframes (e.g., images or derivatives of the images) to the system for use in feature detection, generating specification, and automatic prototyping.

The system can be configured to use the detected features to generate a product specification or statement of work based on the matches. This can be performed automatically.

The feature detection can include a normalization process that is configured to provide adaptation, filtering, or modification of wireframes and/or software display screens of previously developed features for prior customer software application to normalize the visual content so as to aid in the detection and feature matching operations.

A prototype engine can run the prototype by using meta data or structure stored for the features, such as for a particular project, to generate the visual display consistent with the feature. This process can, for example, generate the prototype, that generally simulates the expected user interactive experience, extremely quickly (immediately) in response to the user desired specification and software design by simply pressing a button to be able to see an early version of the desired software in operation. For example, simply by pressing a preview button, the user can immediately cause the display of an operable interactive prototype displayed using screen or window representations. This can be at the initial process stage when a user uses the platform to specify the requirements (communicates the desired software application) and as such can also be given the ability to provide interactive feedback and design refinement with the platform interface on the proposed design requirement (including visual design) at this initial software development or engagement stage. It can also be provided in other situations.

The platform is configured to automatically connect and arrange features (and corresponding screens) to provide the prototype. In some embodiments, this is performed by using an underlying set of inter-feature characteristics information. This inter-feature information can be information that summarizes a history of user interaction involved in creating new software applications using features. The history may involve many different interactions including inter-screen connections. The user or customer can edit the arrangement. An advantage being that the timely and overwhelming task of handling the minutiae of selecting each feature, selecting what it connects to, and how it connects is automatically performed. This can lead to the customer needing only to conduct fine tuning. The use of historical information can provide the capability to automatically and dynamically update how features are interconnected as additional historical information is obtained, aggregated and processed for use. Overall, these are computer-implemented techniques that provide a significant step forward compared to the known processes.

In preferred embodiments, the platform is an online software development platform that is used by the public to engage a company to develop a particular software application for the customer. An example of such a system is illustratively described in U.S. Patent Publication No. 20180107459, by Dugal et al., filed Oct. 17, 2017, which is incorporated herein by reference in its entirety. The platform is preferably configured to provide the user, a potential customer, with the ability to interact with different interactive user interfaces to intuitively specify the requirements for the desired custom software application. The platform can be configured to operate as an application in object code that interacts with the user. The platform preferably includes a repository of existing source code for individual features that have been previously collected, used and/or tested to implement a corresponding feature. This source code can be reused, modified or compiled during the software development to produce the actual software application sought by the user. The platform preferably includes, separate from the source code and object code for the features, object code adapted into the application of the platform (operating and existing in object code) that is configured to be a simulation of an actual corresponding feature (e.g., without the need to compile the code to create the simulation). This provides dynamic live features of the software development platform that are a component of the object code of that application. The platform maintains an association between the integrated object code simulation or interactive representation and the source code for the actual feature to be used in a custom developed application. These are predetermined or preconfigured aspects of the platform. Thus, the system is configured to maintain different modes of a feature, including one that is an object code simulation and one that is the source code for the actual feature for use in a developed application.

The platform can also include a subsystem that communicates with a set of third party software developers to communicate the requirements (via messaging) and to engage the developers to develop additional source code or desired modification that after a query to the existing database of feature source code is determined to be needed or unavailable in the repository, thus requiring the developers to create new code for requirements or selections that are not in the repository (which is communicated via the platform). The platform can also communicate the requirements internally via electrical communications and in response automatically generate or assemble source code that contains the source code for the selected features from the repository. The repository can store different versions of the source code, such as for different operating systems or different end user platforms (e.g., mobile phones versus laptops). As part of the software development process, the platform can display interfaces that require the user to select the operating system and end user platform. The platform takes that selection into account in pricing and/or generating or assembling source code for a customer's actual application.

In operation, in embodiments of the present invention, the features and described inter feature relationship are preconfigured when a user accesses the platform to use wireframes to detect features and select to view the prototype (instantly).

The platform can be configured to allow the user to select automatic detection as a preliminary step in order to specify the requirements for the desired custom software application. In some embodiments, the platform can be configured to allow the user to select features (using a user interface). In response to the feature detection/selection, the platform can use that information to automatically generate pricing, taking into account selected features.

The platform can therefore be configured for the user to perform the design process or a portion thereof. The platform can preferably provide the user with an integrated resource for design and the automatic generation of prototypes or simulations in addition with a streamlined process for software development where there is preexisting common structure between design and development such as by way of correspondence between prototype visualization and designed corresponding source code for the actual software that is part of the platform.

Preferably, the prototyping has limited functionality and is a simulation provided through the interface of the software development platform. For example, a feature to reset a password as a prototype is configured to display the relevant custom application screens, not actually require true login credentials or to send an email reset link. It is focused on the in-software shell interaction.

The term prototype is used herein to refer to a simulation of a desired software application (based on user requirements) graphically provided within a user interface of an online platform by displaying simulated user interfaces within the environment of the graphical interface of an online platform that provides online software development tools such as a software application development platform. The simulation corresponds to a desired actual application. This is so as to clarify that the general usage of prototype can refer to an early or experimental version of an actual software application running, as opposed to a simulation within the interface of the software development platform wherein the prototype process within the software development application is adapted to collect user requirements and specify design characteristics, in particular in present embodiments from digital image analysis of wireframes, related to contents of interfaces, interaction, and flow of the desired actual application for that customer.

FIG. 1 is a simplified block diagram of a distributed computer network 100 incorporating an embodiment of the present invention. Computer network 100 includes a number of client systems 105, 110, and 115, and a server system 120 coupled to a communication network 125 via a plurality of communication links 130. Communication network 125 provides a mechanism for allowing the various components of distributed network 100 to communicate and exchange information with each other.

Communication network 125 may itself be comprised of many interconnected computer systems and communication links. Communication links 130 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 125 is the Internet, in other embodiments, communication network 125 may be any suitable communication network including a local area network (LAN), a wide area network (WAN), a wireless network, an intranet, a private network, a public network, a switched network, Internet telephony, IP telephony, digital voice, voice over broadband (VoBB), broadband telephony, Voice over IP (VoIP), public switched telephone network (PSTN), and combinations of these, and the like.

System 100 in FIG. 1 is merely illustrative of an embodiment and does not limit the scope of the systems and methods as recited in the claims. One of ordinary skill in the art would recognize other variations, modifications, and alternatives. For example, more than one server system 120 may be connected to communication network 125. As another example, a number of client systems 105, 110, and 115 may be coupled to communication network 125 via an access provider (not shown) or via some other server system. An instance of a server system 120 and a computing device 105 may be part of the same or a different hardware system. An instance of a server system 120 may be operated by a provider different from an organization operating an embodiment of a system for specifying an object in a design, or may be operated by the same organization operating an embodiment of a system for specifying an object in a design.

Client systems 105, 110, and 115 typically request information from a server system which provides the information. Server systems by definition typically have more computing and storage capacity than client systems. However, a particular computer system may act as both a client and a server depending on whether the computer system is requesting or providing information. Aspects of the system may be embodied using a client-server environment or a cloud-cloud computing environment.

Server 120 is responsible for receiving information requests from client systems 105, 110, and 115, performing processing required to satisfy the requests, and for forwarding the results corresponding to the requests back to the requesting client system. The processing required to satisfy the request may be performed by server system 120 or may alternatively be delegated to other servers connected to communication network 125.

Client systems 105, 110, and 115 enable users to access and query information or applications stored by server system 120. Some example client systems include portable electronic devices (e.g., mobile communication devices) such as the Apple iPhone®, the Apple, or any device running the Apple iOS™, Android™ OS, Google Chrome OS, Symbian OS®, or Windows Mobile® OS. In a specific embodiment, a "web browser" application executing on a client system enables users to select, access, retrieve, or query information and/or applications stored by server system 120. Examples of web browsers include the Android browser provided by Google, the Safari® browser provided by Apple, the Opera Web browser provided by Opera Software, and Internet Explorer Mobile browsers provided by Microsoft Corporation, the Firefox® and Firefox for Mobile browsers provided by Mozilla®, and others.

Figure 2:
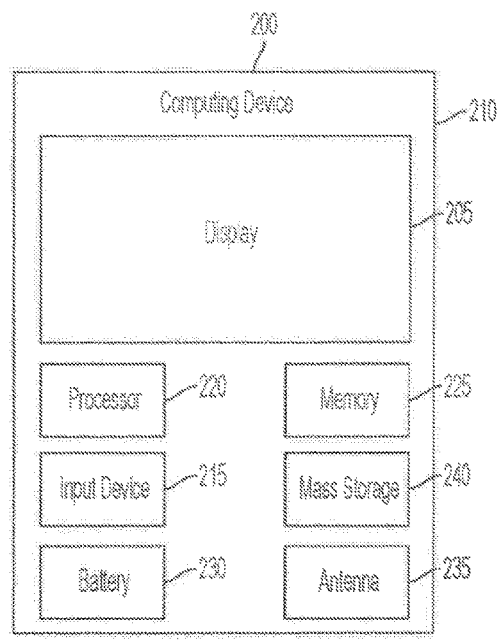
FIG. 2 shows an exemplary computer system such as a client system according to an embodiment of the present invention.

FIG. 2 shows an exemplary computer system such as a client system of the present invention. In an embodiment, a user interfaces with the system through a client system, such as shown in FIG. 2. Mobile client communication or portable electronic device 200 includes a display, screen, or monitor 205, housing 210, and input device 215. Housing 210 houses familiar computer components, some of which are not shown, such as a processor 220, memory 225, battery 230, speaker, transceiver, antenna 235, microphone, ports, jacks, connectors, camera, input/output (I/O) controller, display adapter, network interface, mass storage devices 240, and the like. Computer system 200 may include a bus or other communication mechanism for communicating information between components. Mass storage devices 240 may store a user application and system software components. Memory 225 may store information and instructions to be executed by processor 220.

Input device 215 may also include a touchscreen (e.g., resistive, surface acoustic wave, capacitive sensing, infrared, optical imaging, dispersive signal, or acoustic pulse recognition), keyboard (e.g., electronic keyboard or physical keyboard), buttons, switches, stylus, gestural interface (contact or non-contact gestures), biometric input sensors, or combinations of these.

Mass storage devices 240 may include flash and other nonvolatile solid-state storage or solid-state drive (SSD), such as a flash drive, flash memory, or USB flash drive. Other examples of mass storage include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), battery-backed-up volatile memory, tape storage, reader, and other similar media, and combinations of these.

System 100 may also be used with computer systems having different configurations, e.g., with additional or fewer subsystems. For example, a computer system could include more than one processor (i.e., a multiprocessor system, which may permit parallel processing of information) or a system may include a cache memory. The computer system shown in FIG. 2 is but an example of a computer system suitable for use. Other configurations of subsystems suitable for use will be readily apparent to one of ordinary skill in the art. For example, in a specific implementation, the computing device is a mobile communication device such as a smartphone or tablet computer. Some specific examples of smartphones include the Droid Incredible and Google Nexus One®, provided by HTC Corporation, the iPhone® or iPad®, both provided by Apple, and many others. The computing device may be a laptop or a netbook. In another specific implementation, the computing device is a non-portable computing device such as a desktop computer or workstation.

A computer-implemented or computer-executable version of the program instructions useful to practice the present invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version of the software useful to practice embodiments of the present invention may be stored or reside in RAM or cache memory, or on mass storage device 240. The source code of this software may also be stored or reside on mass storage device 240 (e.g., flash drive, hard disk, magnetic disk, tape, or CD-ROM). As a further example, code useful for practicing embodiments of the invention may be transmitted via wires, radio waves, or through a network such as the Internet. In another specific embodiment, a computer program product including a variety of software program code to implement features of embodiments of the invention is provided.

Computer software products may be written in any of various suitable programming languages, such as C, C++, C#, Pascal, Fortran, Perl, Matlab (from MathWorks, www-.mathworks.com), SAS, SPSS, JavaScript, CoffeeScript, Objective-C, Objective-J, Ruby, Python, Erlang, Lisp, Scala, Clojure, and Java. The computer software product may be an independent application with data input and data display modules. Alternatively, the computer software products may be classes that may be instantiated as distributed objects. The computer software products may also be component software such as Java Beans (from Oracle) or Enterprise Java Beans (EJB from Oracle).

An operating system for the system may be the Android operating system, iPhone OS (i.e., iOS), Symbian, BlackBerry OS, Palm web OS, bada, MeeGo, Maemo, Limo, or Brew OS. Other examples of operating systems include one of the Microsoft Windows family of operating systems (e.g., Windows 95, 98, Me, Windows NT, Windows 2000, Windows XP, Windows XP x64 Edition, Windows Vista, Windows 7, Windows CE, Windows Mobile, Windows Phone 7), Linux, HP-UX, UNIX, Sun OS, Solaris, Mac OS X, Alpha OS, AIX, IRIX32, or IRIX64. Other operating systems may be used.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system useful in practicing the invention using a wireless network employing a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

Figure 3:
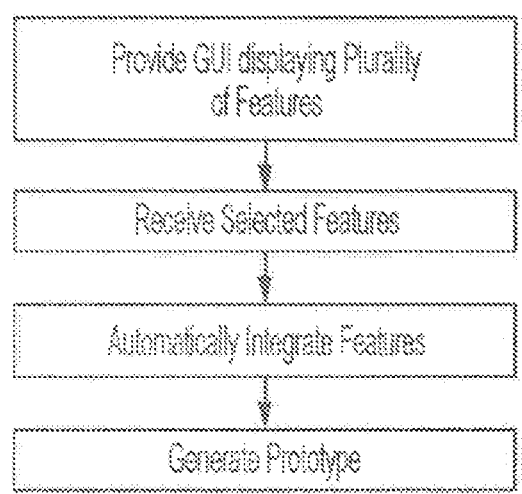
FIG. 3 illustrates a flow chart of an interactive application building process according to an embodiment of the present invention.

FIG. 3 illustrates a flow chart of an interactive application building process 300, according to an embodiment of the present invention. A user may interact from a browser or other application on their client device to participate in the process. The application development system of the present invention packages a set of selected and/or detected features into a functional prototype of software application by setting up and regulating the flow of data between the features based on attributes embedded in each feature.

The system implements a method that includes providing a graphical user interface on a display of a client device, the graphical user interface displaying a plurality of features from a library of features for a custom software application; receiving from the client device, by a server running a software building component, one or more selected features for the software application. The system can be configured to receive wireframes (illustrations of desired displays and/or display flow) and detect, identify, or correlate the wireframes to a set of features. The system can automatically integrate, by a software building component, the one or more features to generate an integrated feature set based on attributes of each of the selected features and an inter-feature rules set, and generating on the graphical user interface an interactive visualization of a navigable prototype of the software application based on the integrated feature set. In some embodiments, the system further comprises customizing a feature by receiving from the client device one or more inputs for modifying attributes for the feature. The system may also further provide for customizing by enabling the addition, subtraction, editing, or reordering of features or the editing of connections between the features.

Figure 4:
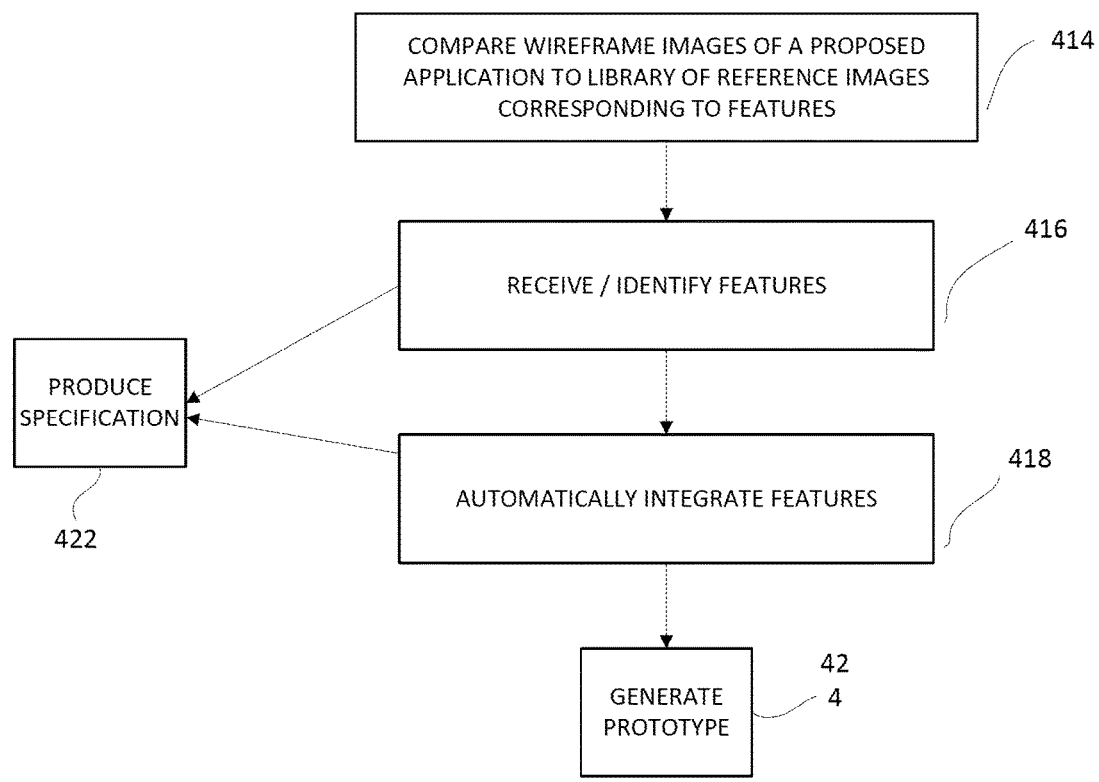
FIG. 4 illustrates a flow chart of an interactive application building process according to an embodiment of the present invention.

FIG. 4 illustrates a flow chart of an interactive application building process 412, according to an embodiment of the present invention. At step 414, the system compares wireframe images (in this context, images should be understood to include graphical representations of an image of a wireframe from which graphic content of wireframe can be found or analyzed) of a proposed custom software application to features such as features available for developing software applications on the system. The system may store data comprising a library of reference images corresponding to features. The data or library can be configured to include images (e.g., JPEG) of one or more display screens of a feature from a set of configured features and/or can include data in the form from which salient visual or interconnection characteristics of one or more display screens of a feature are saved for comparison to wireframe images for detection of features. A comparison is performed using the wireframe illustration(s) and the data of reference images to select, automatically, one more features that are found in the wireframes based on the feature reference images and related data.

At step 416, the system may receive the selected or identified features (e.g., can be a combination of automatically identified features and features selected by a user). At step 418, the system automatically integrates the received features. At step 422, the system can, in response to receiving the identifier features and/or receiving how the features are integrated, generate a specification or state of work for the custom software application. The process can involve determining source code available for the feature or use an estimate of the integration and further development required for the project.

At step 424, the system can generate a prototype automatically to provide an instant prototype to the user for interaction. This can be a rapid process wherein a user can load images of their desired application and in response the system automatically identifies the desired features of the application and automatically generates a functional prototype using the identified features.

Figure 5:
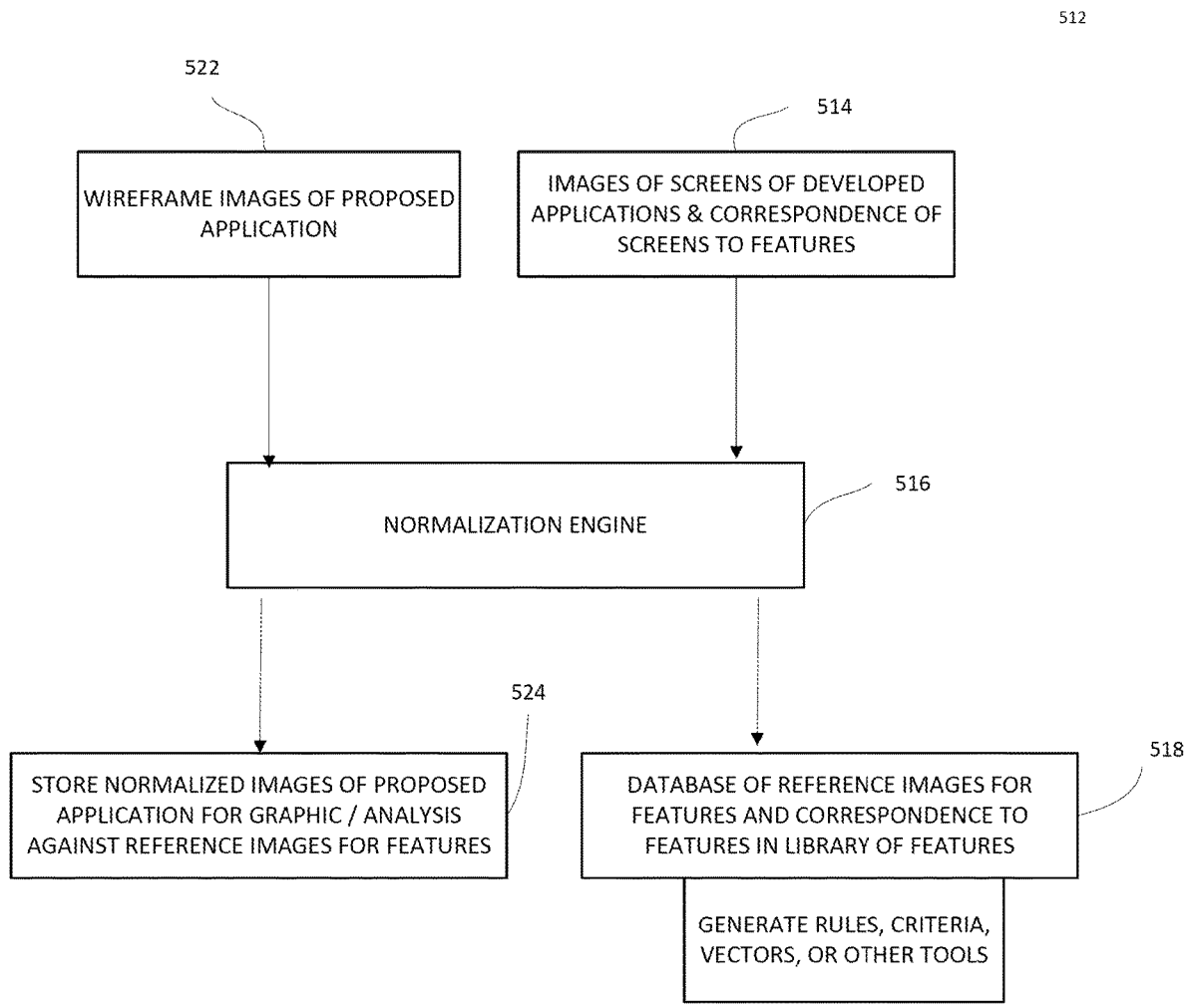
FIG. 5 illustrates a flow chart of an interactive application building process according to an embodiment of the present invention.

FIG. 5 illustrates a flow chart of an interactive application building process 512, according to an embodiment of the present invention. Process 512 is an example process involved in configuring the system to perform the comparison to identify correlations or perform conversion between wireframe illustrations (by UI designer or customer) and system features. At step 514, the system may receive and store in non-transitory storage, images of display screens, where the display screens are from functional object code generated software, and corresponding characteristics of the display screens to features. For example, the system may generate images from display screens implemented for the following features: login, profile, map, gallery, and product view. The images may be generated by using a print or display screen, e.g., automatically. The display screens can be from developed custom applications or modules. The images can be reference images from the comparison process. The system would store data providing correspondence to features to allow for a conversion or correlation.

At step 516, a normalization engine may be implemented. At this step, the images from the display screens can be subject to a set of graphical processes to prepare them for the comparison process. Aspects of the process can be configured by the user.

At step 518, in response to the processing by the normalization engine, a database of reference images for features and correspondence to feature in the feature library (available set of features) is stored for use in the comparison and detection process. Step 518 may include a process in which the references images are processed to generate rules, criteria, vectors, or other tools for detecting a correlation or correspondence from graphical content (and interrelationship of content) to a respective feature. For example, the location and arrangement of two boxes in a wireframe (e.g., stacked vertically and of the same size) can be a rule that can automatically be applied to correspond a wireframe to a login feature. In some embodiments, the system may rely on text detection as part of determining a corresponding feature if desired, but it can be performed without it.

At step 522, the system can be received from a new customer or that customer's designer, wireframe images of the customer's proposed application. The system can be configured to receive PDFs or other images and perform an operation as part of the receiving process such as to receive files and convert to an image format such as JPEG. At step 516, a normalization engine may be implemented. At this step, the images from the display screens can be subject to a set of graphical processes to prepare them for the comparison process. Aspects of the process can be configured by the user. At step 524, the system can store normalized images of the proposed application for graphical analysis against reference images of features.

Figure 6:
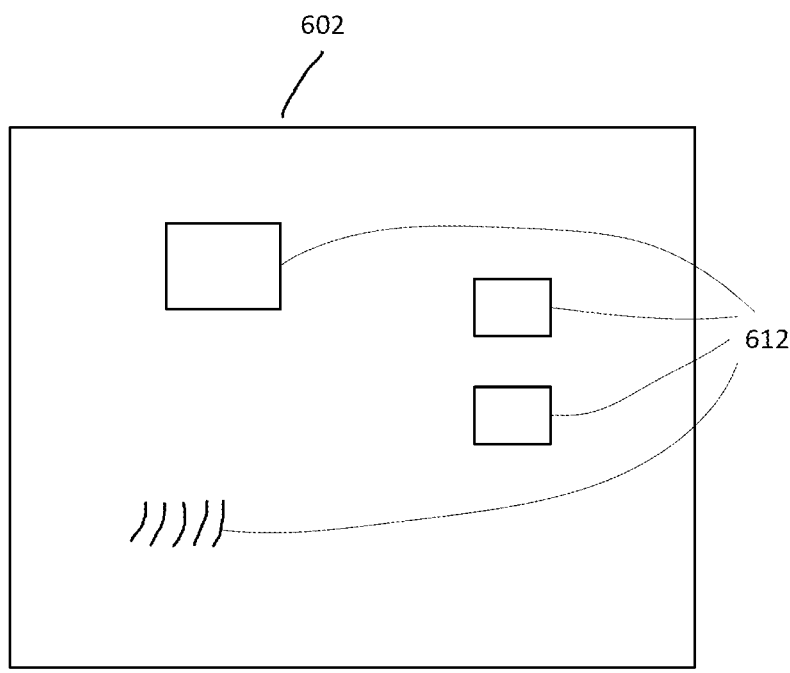
FIG. 6 illustrates an example of a wireframe as part of the process according to an embodiment of the present invention.
Figure 7:
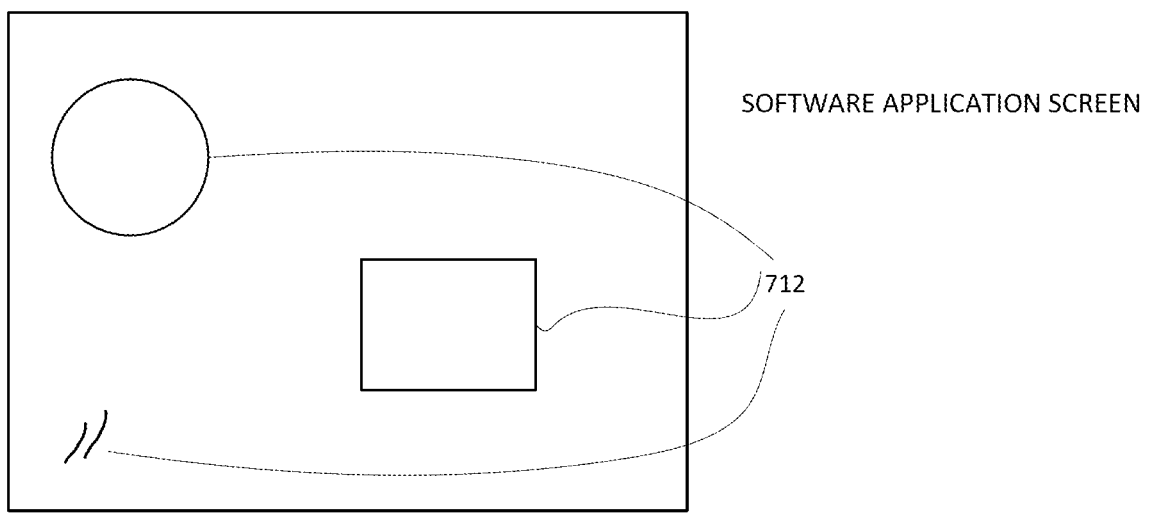
FIG. 7 illustrates an example of a display screen as part of the process according to an embodiment of the present invention.

The system can receive as input images 602 of FIG. 6, a first image representing the original design of a user interface, and can receive or store for use a database of one or more reference images 702 (corresponding to features such as product view) of actual user interfaces, that is the application's render of the original design of the user interface for another customer or as a previously produced base building block. The original design image is the image of the user interface as conceived before or during the development of the application by graphic artists or developers, while the reference image(s) are previously generated without use or involvement of this customer's original design. The design image can include one or more visual elements (see FIG. 6, 612). The image 602 may be generated through a variety of means, such as a graphic design application, a CAD application, or any other means of generating a picture of the intended design. The user interface image 702 or application render 702 is preferably a screenshot of the application. The user interface 702 may also otherwise have been generated or rendered by the application, provided that it is a representation of the user interface as displayed on the screen. Each of original design image 602 and the application's image or screenshot 702 can be in a variety of image file formats. These include Windows Bitmap (bmp), Portable Image Formats (pbm, pgm, ppm), Sun Raster (sr, ras), JPEG (jpeg, jpg, jpe), JPEG 2000 (jp2), TIFF files (tiff, tif), and Portable Network Graphics (png), among others.

The images can be received and processed by a normalization engine 516. The normalization engine 516 is configured to format or convert the images into a format that enables comparison. For example, the normalization engine 516 compares the pixel dimensions of the original design image 602 and the screenshot 702. If the dimensions are not identical, the screenshot 702 can be resized to match the dimensions of the original design image 602. The normalization engine 516 may also change the format of an image to match the other or of both images to match the preferred image format of the normalization engine 516. In some embodiments, images are converted into PNG format. The converted images can be used by the comparison engine 414.

The comparison engine 414 is first configured to locate and detect similarities (features that match or have matching graphical characteristics) in graphical content (and/or interrelationships) between the wireframe image (original design image 602) and the image 702 and many other images of display screens for features (stored for use in the comparison and conversion of images to features). To that end, the comparison engine 414 compares the received images to generate a similarity map. In some embodiments, the application may run on a server as a web app, and may include a visual interface for this feature and may be displayed in a conventional browser on a client computing device.

The comparison engine may generate the similarity map (or, more broadly, comparison between wireframes and library of display screens) using a variety of image comparison techniques. In one embodiment, the similarity is determined by performing a pixel-wise comparison between images. Specifically, the comparison engine can traverse the content images using a Structural Similarity Index Method (SSIM) algorithm on every pixel of the images. SSIM is a statistical method to comprehensively evaluate differences between images and is described in Wang, Zhou & Bovik, Alan & Sheikh, Hamid & Simoncelli, Eero (2004), *Image Quality Assessment: From Error Visibility to Structural Similarity. Image Processing, IEEE Transactions* on 13. 600-612. 10.1109/TIP.2003.819861, which is incorporated herein by reference in its entirety. In this embodiment, the method as implemented employs a sliding window over the entire frame to calculate a local SSIM for each pixel. The SSIM analysis yields three measures of local similarity for each pixel: luminance similarity, contrast similarity, and structure similarity. Each pixel similarity measure can serve as a basis for a map, and the luminance map, contrast map, and structure map can be generated. In some embodiments, the user may select to display each of the maps. The combination or superimposition of all three maps yields the discrepancy map. In other words, the discrepancy is made of pixels, each having three dimensions or similarity measure: luminance, contrast, and structure. In some embodiments, all graphical elements are converted to black/white and the process relies on the graphical similarities of the content without evaluating luminance, contrast, or color.

In some embodiments, user-controlled parameters can be provided that affect the comparison. For example, a scope parameter can determine the resolution of the detector: a sharp scope can be used for small elements, such as characters, small icons. A blurred scope may be employed for big elements. Threshold value is another parameter that may be provided to the user. The threshold value determines the level of similarity between the design image and the screenshot that will be detected as a match. Threshold thus varies between lenient and strict. Slides or other control means can be provided on user interface to enable the user to change each parameter.

Figure 8:
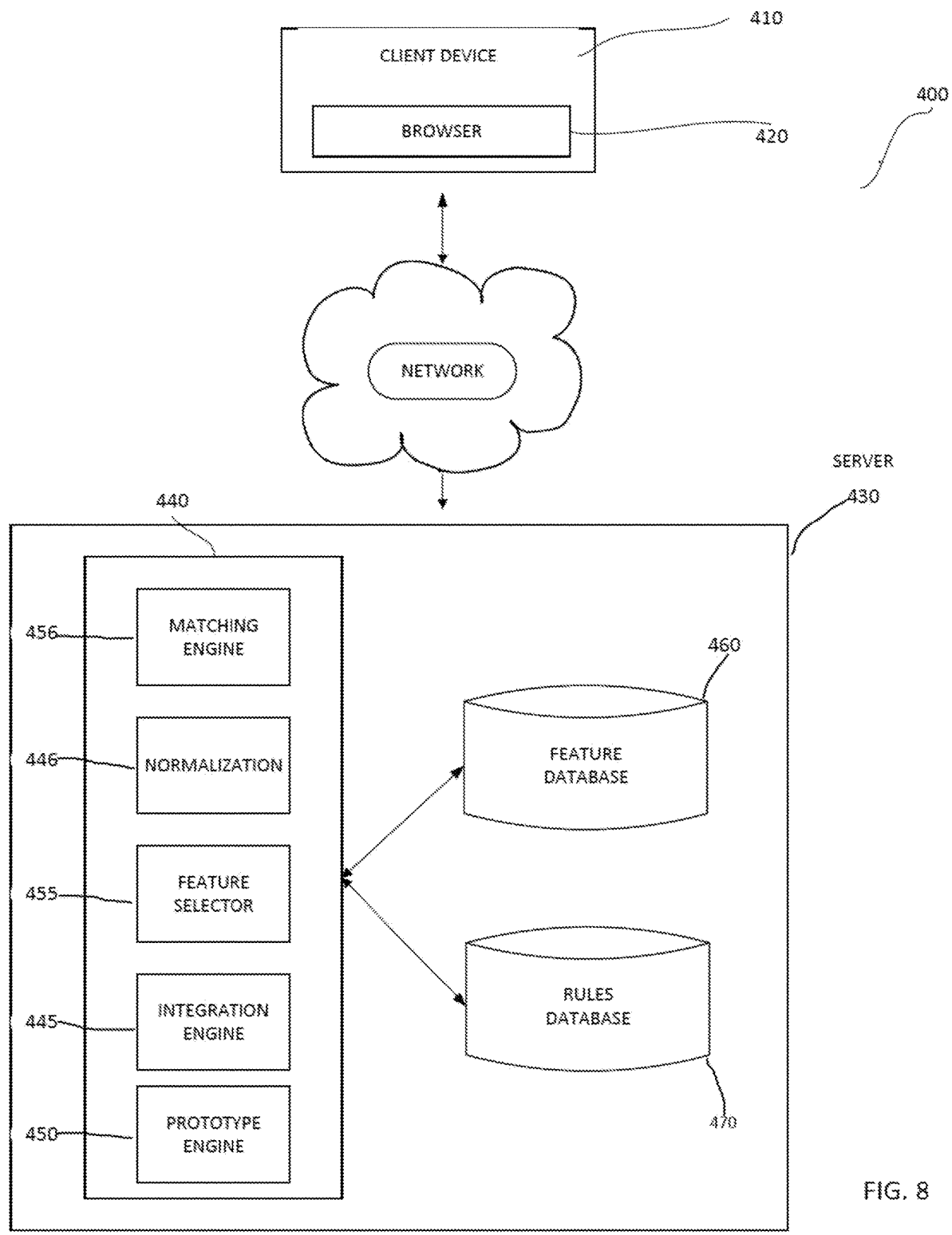
FIG. 8 illustrates a system for developing software according to an embodiment of the present invention.

FIG. 8 illustrates a system for developing software according to an embodiment of the present invention. The system includes an application development software application 420 installed on an electronic device 410 and a builder software application 440 implemented on one or more servers 430. The electronic device 410 is preferably a desktop computer that can communicate with a server via mobile networks or other wireless networks. Each of the electronic devices and servers is a computer system that includes a microprocessor and volatile and non-volatile memory to configure the computer system. The computer system also includes a network connection interface that allows the computer system to communicate with another computer system over a network. Each software application may also be used independently or in conjunction with another software application to strengthen or supplement functionalities of the other software application.

The builder application 440 installed on the server 430 maintains a library of features for a software application. The library of features may be stored in a database 460. Database 460 can include data comprising reference images and correspondence to features in the library. The builder application 440 is configured to receive selected and/or detected features and integrate the selected features into an integrated build card and generate an interactive visualization of a prototype to the software on the client device. The builder application further maintains a rules database 470 configured to store and update rules governing interactions including connections between features of the library.

The software development application 420 is configured to provide a graphical user interface that enables a customer to select and customize a set of features as part of a build card for building an early prototype of the customer's desired application for inspection and fine tuning by the customer. In some embodiments, the software development application 420 is a web application provided by the builder application on the server and configured to run in a conventional browser. In a preferred embodiment, the software development application is the conventional browser 420 configured to access an application development website provided by the server. As discussed, the software development application 420 can provide a user interface or software mechanism to receive images of wireframes for a desired custom software application.

Feature database 640 can also include source code for each of the plurality of available features. The saved source code provides a repository of source code for available features that the platform can use to generate object code for the actual application (e.g., based on the selected operating system) and/or to send the source code to select third party software developers to perform desired integration or modification based on customer specified requirements. The prototype engine 450 preferably uses object code and related data for corresponding features (e.g., without using or compiling the source code for actual implementation) to provide simulation of a set of specified requirements and the ability to interact to arrange or rearrange graphical elements or interface interactions. The simulated features may be based on the source code from the repository in database 640. Preferably, the live feature provides greater flexibility and efficiency. Matching Engine 456 is configured to process wireframe images and use the database to find that wireframe images include certain features based on similarities found between wireframe images (and/or their flow) and images of the developed applications (library of reference images that are stored in association with a corresponding feature). Normalization engine 446 is also discussed herein.

Figure 9A:
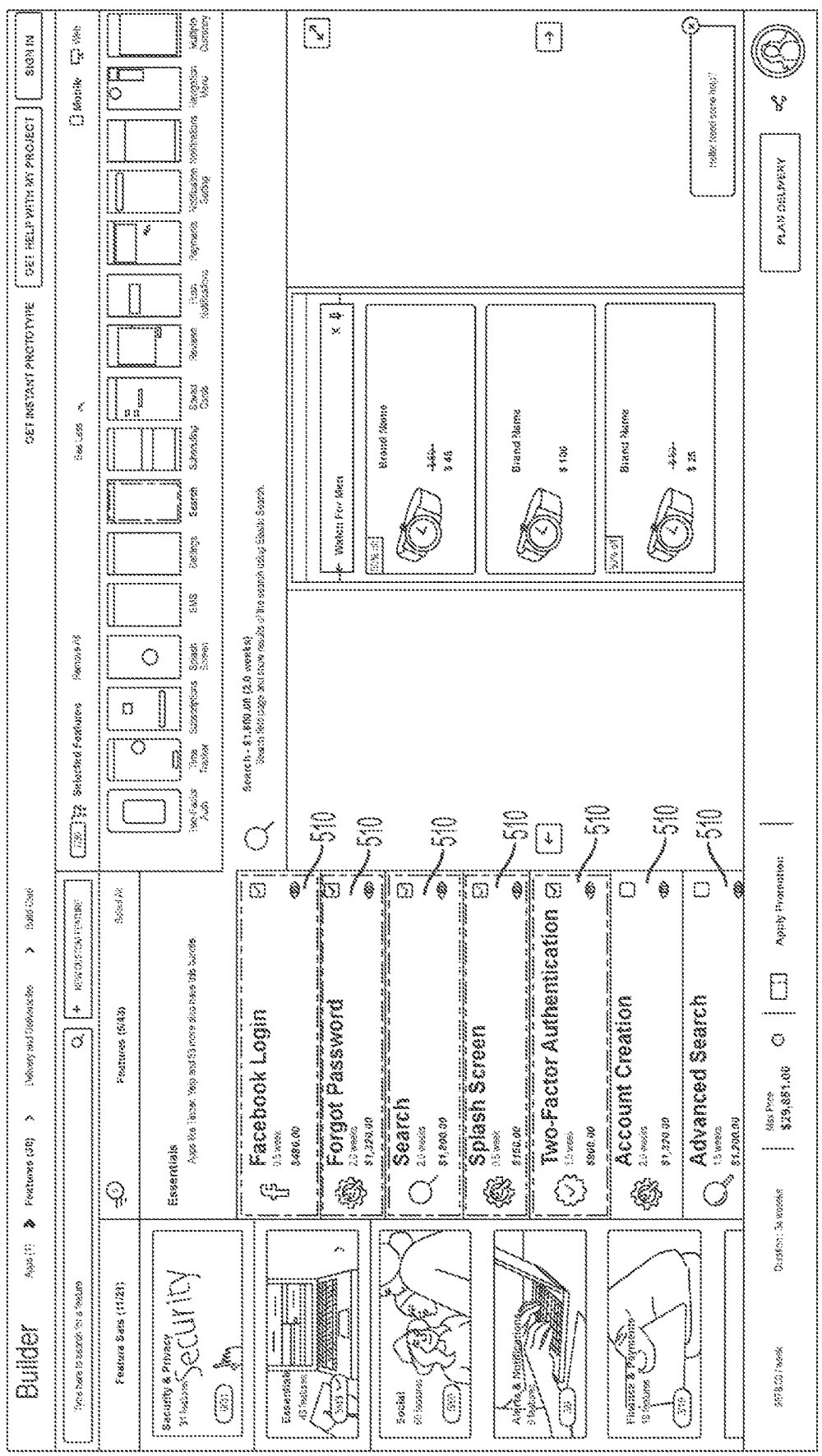
FIG. 9A illustrates an exemplary graphical user interface according to an embodiment of the present invention.

FIG. 9A illustrates an exemplary graphical user interface 500 according to an embodiment of the present invention. The graphical user interface may be displayed in a web browser of a client computing device as part of a web page served by a server. The graphical user interface of embodiments of the present invention is configured to enable a user to select from a library of software features 510 to build a software application. The library of features 510 may be presented as a set of icons, a list, a drop-down menu, or any other means of presenting information on a graphical user interface. As discussed, the system can be configured to receive the wireframe (such as via an API of a wireframe preparation application), perform processing to enable comparison to images of display screen for features, and in response, convert the wireframe to a set of features, e.g., a set of interconnected features. In some embodiments, the graphical user interface can display the library features with the identified features selected for review and edit by the user.

A feature of the software application is a function or set of functions for the application. Conceptually, the feature is the atomic unit of the software project, according to embodiments of the present invention. That is, a feature is an independent unit of predefined functionality that comprises the basic building block of the software according to embodiments of the present invention. Accordingly, a feature is the smallest unit of the desired software application that the customer can employ (or need conceptualize). Further, a feature can be employed in disparate applications with minimal to no change to its core functionality, as will be described further down in this specification. This modular nature of the feature enables embodiments of the system of the present invention to build a prototype merely by logically connecting a selected set of features. In some embodiments, source code for the application or an intermediate representation thereof may be collected or assembled (and saved) based on the prototype. Embodiments of the present invention thus enable the user to select a set of features to be automatically assembled into a working prototype to serve as a basis for an application.

Functionally, a feature includes one or more screens that are logically linked and provide a particular function or set of functions for the application. For example, for a mobile application, a feature's interface may comprise a single screen or a set of logically linked screens, each of which may be invoked from another screen of the set. For a desktop application, a feature's interface may comprise a screen, a set of screens, a frame embedded in a screen provided by another feature, or combinations thereof. Each screen of the feature may exhibit one or more display regions and one or more interactive regions. The display regions serve to display content, whereas the interactive regions serve to interact with a user of the application, as will be described further in this specification. Metadata associated with each feature governs how each display region and region of the feature connects to other features of the library of features. That is, a feature's metadata controls which other features it may call or be invoked by.

At the code level, a feature may represent one or more blocks of software code. For example, a feature may represent a set of objects and data configured to provide a particular function or set of functions to the software application. Thus, the one or more blocks of code may be compiled into one or more object files corresponding to the feature during the software build. The object files may be linked with other object files of other features during the software build according to the configuration of each feature to provide executable code for the application. In the alternative, the feature may correspond to one or more object files or a combination of blocks of source code and object files. For example, a feature at the code level may represent a combination of pre-processor directives, source code, object code/files, including from various libraries, standard and otherwise.

A feature may include a functionality that can be implemented in a modular fashion and that can be interchangeable between multiple software applications. For example, a feature that requires a user of software application to login (or a login feature) can be implemented using the same code and screen or interface across multiple software applications. Other features may require the same core code across multiple applications and platforms, but differ in details. For example, an Account Creation feature may differ in details from one application to another depending on the information that the account creation requires from the user. To that end, the software development platform of the present invention enables the user to customize a feature without modifying its core code and functionality and therefore without affecting its interchangeability between software applications.

Each feature provides an additional means to process data and/or interact with other applications and users. In the context of prototype generation for presenting a workable graphic demonstration of a prototype through a platform such as a browser, embodiments of the present invention do not necessarily need to generate source code or assemble or generate object code from source code. In operation, the system will be operated as a software application that can interact with data, store and modify data, and have the application (running in object form) generate the prototype for interaction with the user via a browser, for example.

Features of the software application may include, for example, Account Creation, which enables the application to have users set up an account by filling out personal details on a form; Location, which provides the application access to the mobile device's location functions; or Push Notification, which enables the application to send notification to users when the application is closed. Typically, features provided in the graphical user interface for selection may be grouped by types of features. For example, the interface may provide a bundle of features deemed "Essentials" (which includes, for example, Account Creation, Search, or Two-factor Authentication), a "Finance & Payments" set (which includes Payments, Centralized Billing, or Automatic Renewal), or a "Customer Insight" set (e.g., Review or Polling features).

Figure 9B:
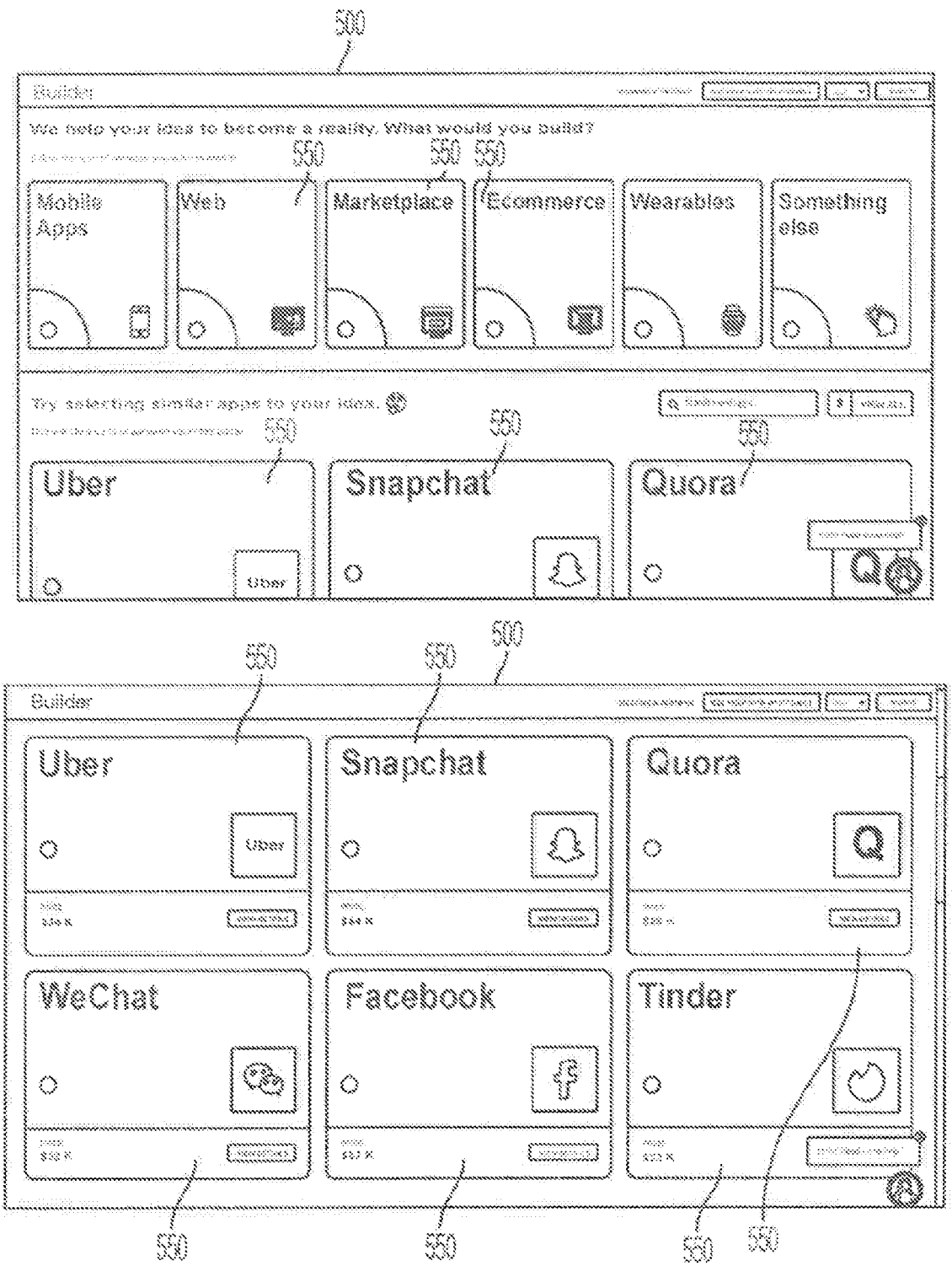
FIG. 9B illustrates graphical user interfaces displaying a library of templates, according to an embodiment of the present invention.

In some embodiments, a subset of the library of features may be organized in pre-organized sets called templates. FIG. 9B illustrates graphical user interfaces 500 displaying a library of templates 550, according to an embodiment of the present invention. Each template 550 of the library provides the basic functional architecture and visual layout of the software project. In particular, the template 550 provides a predefined and customizable basic process flow between a set of predefined and customizable features or functions of the software application. The library of templates 550 may be displayed on the graphical user interface 500 as a set of icons, a list, a drop down menu, or any other means of presenting a set of information on a graphical user interface. Based on the automatic identification of features from wireframe images, the system can also select a template to suggest to the user that they can include additional features that were not identified by the system.

In the embodiment illustrated, the templates 550 are grouped by types of software, such as mobile applications for mobile devices, web applications for websites, marketplace applications that help buyers and sellers transact in real time, e-commerce application, applications for wearable devices such as Apple watches or Google wear, or any other types of applications that may be available on consumer devices. In the embodiment illustrated, the graphical user interface 500 further provides examples of templates within each grouping of templates. For example, the mobile application grouping may include a list of mobile application templates such as Uber, Snapchat, Quora, Tinder, or other popular mobile applications that a customer may want to use as a model to communicate requirements for their own application. A social media grouping for templates may include Facebook, Snapchat, Instagram, and templates of other social media applications. It should be noted that Applicant is not affiliated with the providers of the above applications and services whose structures may provide bases for templates in some embodiments.

After the user has selected a template 550, the user is provided with the opportunity to customize the software project by adding features to or removing features from the template. In some embodiments, the interface may display a set of pre-selected additional features specifically corresponding to the template. For example, if the chosen template is that of a social media app, the user may be provided with additional relevant features such as Private Messages or Take Photo. Thus, the system enables the user to build software by either selecting features individually (e.g., "a la carte") or selecting a predefined set of features or a template, building upon the template by adding or subtracting features to form the software project.

Referring back to FIG. 8, in some embodiments, the builder software 440 on the server 430 may further comprise a feature selector 455 configured to select a set of features based on input from the user. In such embodiments, the client device 410 may prompt the user with various questions for specifying the type of software application and broad set of features desired, rather than presenting the user with a list of specific features. The feature selector 455 is configured to translate the user's input into a set of features to be integrated to form the target software application.

After the selection of features, or the selection of a template and, if desired, a set of additional user-selected features for the template on the graphical user interface, the features are transmitted to the server 430 from the client computing device 410. The template would be understood as discussed herein to include a set of predetermined interconnected features that correspond to a particular model. As described above, the selection of features may also be generated by a feature selector 455 that receives as input answers to prompts from the user interface and generates a selection of features therefrom. Upon receiving the selection of features from the client computing device 410, the builder application 440 transmits the set of selected features to the integration engine 445. The integration engine 445 is configured to assemble the selected features into an integrated build card of the software application. Specifically, the integration engine 445 is configured to receive a set of features, identify new or additional features from the library that may be required by the selection of features, automatically generate connections between the features of the set based on rules from the rules database and the attributes of each feature, and provide an editable visualization of the set of interconnected features or integrated build card. Elements of a feature that enable its connections with other features to form the prototype of the application are described next. The rules can include strength of feature associations, prioritized list per feature, conditionally based on other selected features, or association based on phase of application use (e.g., checkout versus shopping), and other rules, or combinations thereof.

Figure 10A:
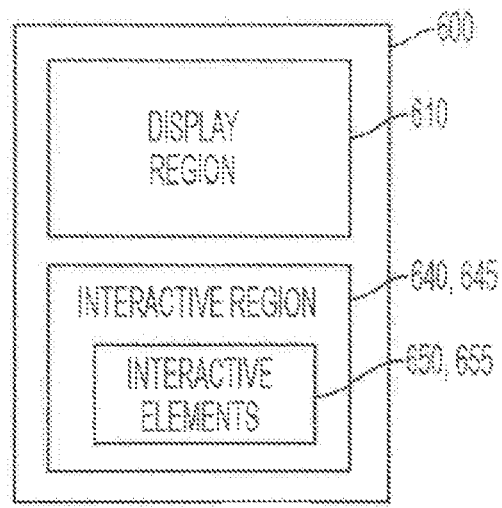
FIG. 10A illustrates a feature as a displayed screen of an application according to an embodiment of the present invention.

FIG. 10A illustrates a feature 600 as a displayed screen of an application according to an embodiment of the present invention. As previously described, a feature 600 may include one or more screens and the illustrated feature comprises a single screen. The feature screen may include one or more display regions 610 and one or more interactive regions 640 (only one of each is shown to simplify the figure). The display regions 610 serve to display content relevant to the feature. The display region 610 may display text, animations, images, videos, or any information configured to be displayed by the feature of the application. The interactive regions 640 host interactive elements 650 that enable the user to interact with the application. Two types of interactive elements 650 are provided: input elements, and navigation elements. Input elements enable the user to provide information in the application. An input element may be a text box, a drop down menu, a radio button, and other forms of input interface elements. The navigation element enables the user to navigate to another screen in the application. In some embodiments, an interactive element 650 may be both an input element and a navigation element.

A particular type of interactive region 640, called hotspot 645 herein, is configured to host a type of interactive element 650 that serves to call another feature. That is, some interactive elements 650 are links or icons in a source feature configured to activate a target or destination feature of the application (which typically involves displaying another screen) when actuated. These interactive elements 650 configured to call another feature are called sidekicks 655 herein.

Figure 10B:
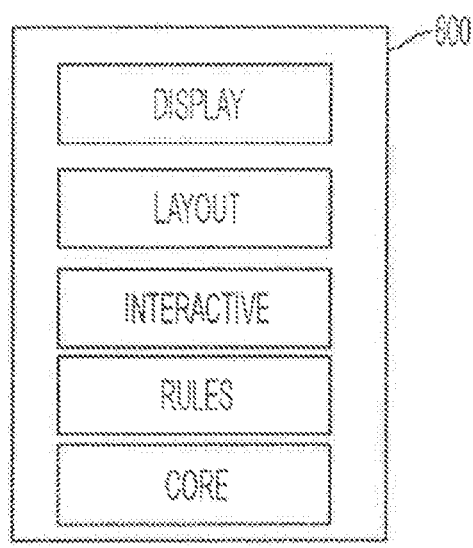
FIG. 10B illustrates a representation of a feature according to an embodiment of the present invention.

FIG. 10B illustrates a representation of a feature 600 according to an embodiment of the present invention. The feature 600 is illustrated as a data structure stored in a database. The feature 600 comprises a layout element that defines the layout of the feature screen, a display element that defines the functions of the display regions of the feature screen, an interactive region element that defines the functions of the interactive regions of the feature screen (e.g., interactive elements and hotspots), rules element governing how the feature may be called, and a core function element that regulates the substantive functionality of the feature (what it actually does).

Figure 11:
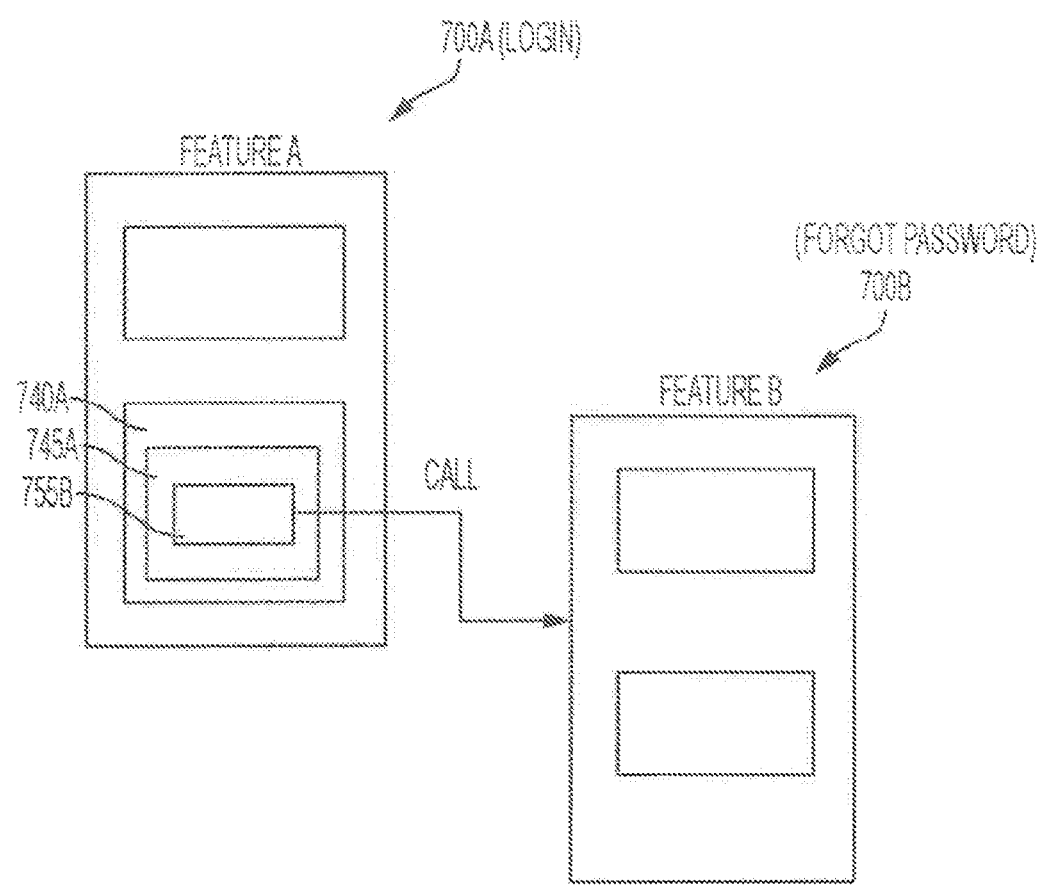
FIG. 11 illustrates two features as displayed screens, according to an embodiment of the present invention.

FIG. 11 illustrates two features 700A and 700B as displayed screens, according to an embodiment of the present invention. The first feature 700A comprises a hotspot 745A in one its interactive regions 740A that hosts a sidekick 755B for the second feature 700B. Actuating the sidekick 755B in the hotspot 745A calls the second feature 700B. For example, the first feature 700A may be a Login feature of an application. The sidekick 755B hosted by a hotspot 745A on the Login feature may be a sidekick of a Forgot Password feature 700B, which is configured to call a Forgot Password feature 700B. Actuating the Forgot Password sidekick 755B (whether by clicking, long-pressing, swiping, or by any other action allowed and specified by the sidekick) thus activates the feature 700B.

Figure 12:
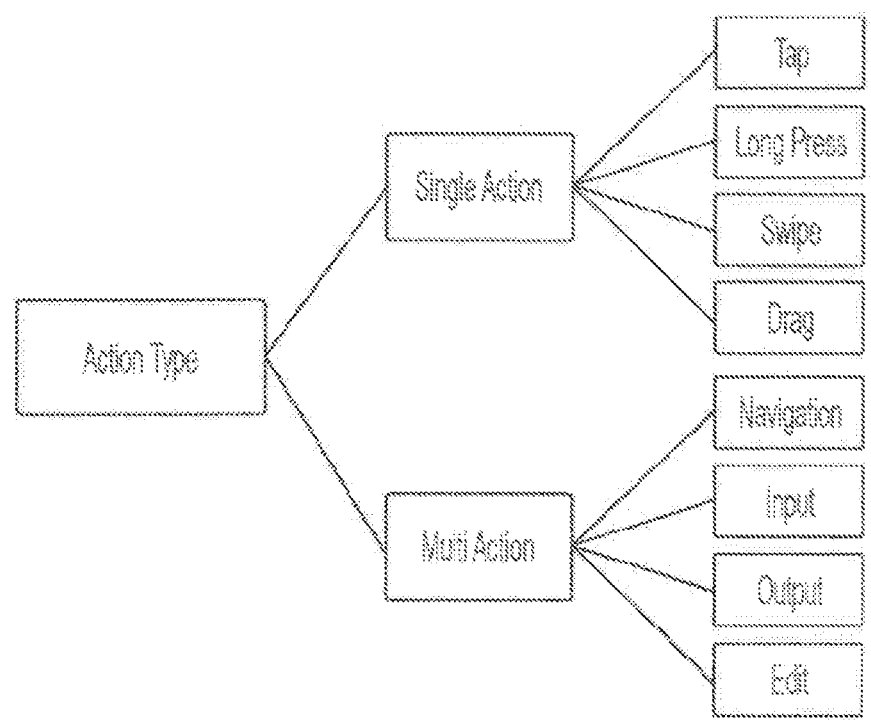
FIG. 12 illustrates an exemplary hierarchy of attributes for a feature that governs the feature's interaction with other features, according to an embodiment of the present invention.

A feature comprises a set of attributes that govern how it may be called. These attributes may be stored as metadata associated with each feature. FIG. 12 illustrates an exemplary hierarchy of attributes 800 for a feature that governs the feature's interaction with other features. In particular, this hierarchy of attributes 800 governs the action type that can call or activate the feature (as a target feature or destination feature) from another feature (source feature).

The Action Type for the subject feature can be a single action or Multi-Action. A single action may include a tap, a long press, a swipe, or a drag. Multi-Action may comprise Navigation, input, output, and edit. Thus, if the action type for an exemplary feature were Single Action, Long Press, such a feature could only be linked to by a long press on an interface element linking to the feature.

Referring back to FIGS. 10A and 11, a hotspot 745 in the interactive region 740 of a feature also comprises a set of attributes that indicate which features the hotspot 745 may invoke. More specifically, the attributes indicate the types of features whose sidekicks 755 or icons the hotspot 745 may host. Accordingly, the hotspot's set of attributes mirrors features' metadata that govern how the features may be called. For example, a hotspot's attributes may be single action, long press. This means that only sidekicks (or links) 755 of features that match these attributes (i.e., single action, long press), can be hosted in the hotspot 745 and therefore be called from it.

Each feature thus may comprise two sets of attributes that govern how the feature may interact with other features: a first set of attributes in the feature's metadata that determines its behavior as a destination feature, that is, which types of actions may be invoked from a hotspot to call the feature, and a set of attributes that determines its behavior as a source feature, that is, which types of features one or more hotspots of the source feature can call. Table 1 illustrates an exemplary set of action type attributes for a feature or for a hotspot of a feature.

TABLE 1

| Single Action | Tap | No |
| --- | --- | --- |
| | Long Press | Yes |
| | Swipe | No |
| | Drag | No |
| Multi-Action | Navigation | No |
| | Input | No |
| | Output | No |
| | Edit | No |

The integration engine 445 (shown in FIG. 8) is configured to assemble or integrate the set of selected features into an integrated build card for the application based on the attributes for each feature (e.g., as described above) and a set of rules governing the inter-feature relationships or associations (as stored in the rules database). To automatically integrate the features of the application, the integration engine 445 accepts as an input the set of features received from the client device (which may include the selected template and any additional features). Specifically, the integration engine 445 receives a build card, which is an instance of the set of features that is instantiated from the selected set of features received from the development application 420 on the client device 410, and generates an integrated build card based on the received build card and the inter-features rules set.

The integration engine 445 may retrieve the set of rules used to integrate the features from a rules database 470 configured to define and store the relationships between features of the library of features. The integration engine 445 can be configured to store common feature interconnections or feature flows and present the user with suggested interconnections or flows. This can include suggestions of proximity of features to each other within a flow of screens or pages in the application.

In some embodiments, the relationship (e.g., connections or flow) may be stored in terms of probability of connections between the features 910. Other methods for storing or representing dependencies or relationships between features in the database are contemplated.

Thus, for each feature, the integration engine 445 automatically identifies which source features should be provided with links to the feature, based on the rules database (i.e., the graph database, in some examples). The integration engine 445 may also automatically determine destination features whose links the feature should host. The integration engine 445 is further configured to identify new or additional features (i.e., features not selected by the user) that the rules database indicate may be associated with features that were selected by the user. Further, for each feature, the integration engine determines links to which functions of the feature, and the form of those links in the source feature based on the attributes of the source and destination. For example, in an eCommerce application whose feature selection by the user include a Product feature that displays a product for sale and a Checkout feature to checkout purchases, the integration engine 445 may automatically determine the Product feature should call the Checkout feature based on the rules database because the rules database associates the Checkout feature with the Product feature; this may mean that a link to the Checkout feature should be placed in an interactive region of the Product feature to provide the ability to check out. Further, within each source feature, the integration engine 445 may cause the feature to provide a logical and optimal layout for the screen (e.g., size, shape, number, functionality of display regions and interactive regions) to accommodate the destination features whose links the source feature hosts, based on the attributes of the source and destination features. Thus, the integration engine 445 may automatically determine that the checkout link should be in the form of a button rather than a check box.

Figure 13:
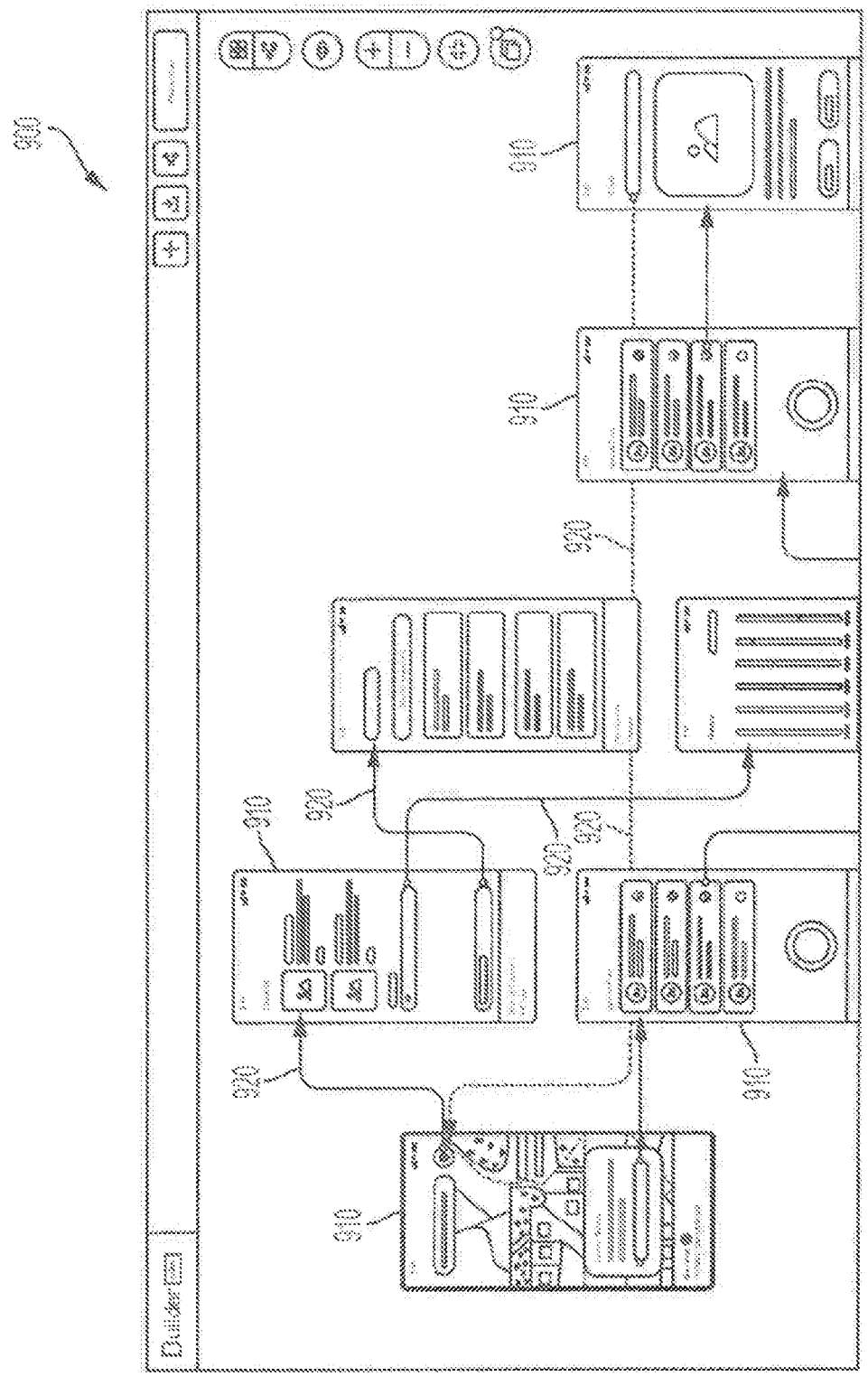
FIG. 13 illustrates a screen flow view of an integrated build card according to an embodiment of the present invention.

The integration engine 445 subsequently generates a screen flow view of the integrated build card on the graphical user interface of the client device. FIG. 13 illustrates a screen flow view of the integrated build card 900 according to an embodiment of the present invention. The screen flow view illustrates the software project as a set of features 910, each represented by one or more screens 910. The features 910 of the screen flow consist of the features of the selected template and set of additional selected features that are logically and automatically connected together by the integration engine 445 based on the rules database 470 and on the attributes of each feature 910 of the feature set. The screens 910 are linked by connectors 920 such as lines or arrows 920 that indicate the interaction between the features 910. The connectors 920 may be of various types and colors to represent different types of interactions between the screens 910. For example, a connector 920 of a certain color may indicate that the destination feature is called by a single action gesture (e.g., a tap), whereas a connector of another color may indicate a multi-action gesture. In addition to the color of the connectors, other visual indicators (thickness, dashed lines, etc.) may serve to indicate the type of interaction between the source and the destination feature. The screen flow view enables the developer to visualize the interactions between the various features 910 of the application.

The system can receive images and automatically generate a prototype from features found in the images to provide quick resource for customers in developing their new custom application.

The system further enables the user to customize the prototype by editing the screen flow. Connections or navigation 920 between the features or screens 910 can be altered by changing the source of an arrow, its destination, or both (interactively using graphics), as well as the type of arrow (type of connection). When a new connection is formed 920, the integration engine automatically determines and provides the appropriate link (i.e., the type of connection) to the destination feature in the source feature based on the attributes of the source feature and destination feature. The integration engine may further adjust the layout of the destination feature to accommodate the link. The attributes of each of the source and destination feature may govern which connections 920 are possible. For example, if a particular feature can only accommodate three links to destination features (for example, because of limited space in the interactive regions of the source feature), the screen flow may not allow the addition of a fourth destination feature link to the source feature. Alternatively, the source feature may switch to a different type of interface elements (e.g., from a set of icons to a drop down menu) to accommodate the additional link. The customer or user may also edit individual features 910 to modify the layout, change the size and shape of the display and interactive regions and elements, add or subtract the same as well as links to destination features.

The integration engine 445 saves each edit of a feature and alteration of the connections 920 or navigation between features 910 in the rules governing the relevant features of the integrated build card. In particular, the integration engine translates each edit to a feature on the interface into the database entry for the instance of the feature. This enables the integration engine 445 to build the integrated build card from a set of edited features that reflect the edits of the customer (e.g., changes to the features and connections between the features) made on the screen flow as described above. After the next integrated build card is built, reflecting the changes made on the screen flow, the user may further alter the screen flow (which is regenerated based on the saved edits) to revise the application project and build a subsequent prototype. This iterative process enables the customer to observe the result of each change and progressively fine tune the project to meet their specification.

Figure 14:
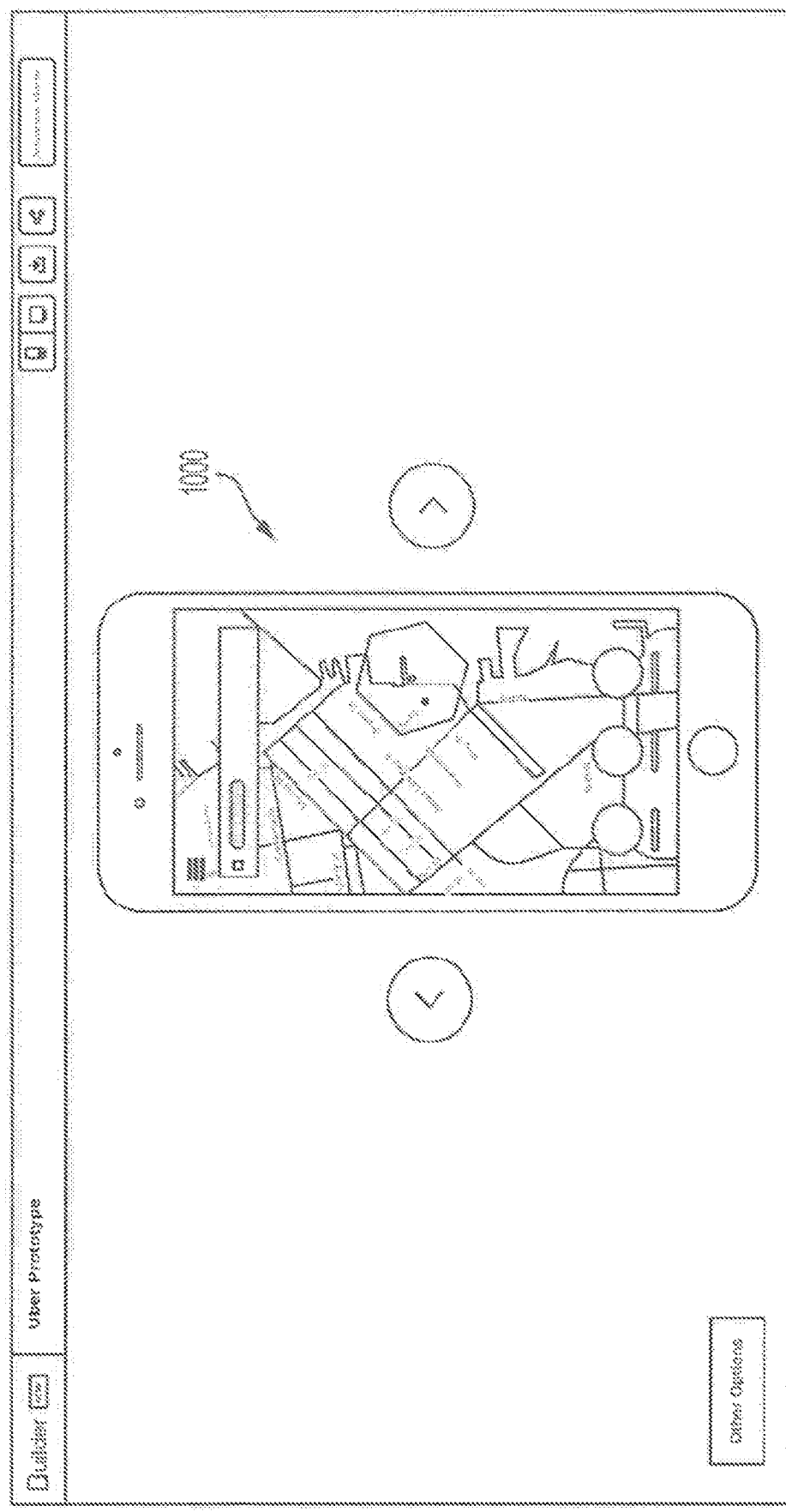
FIG. 14 illustrates a screenshot of a prototype of the software application according to an embodiment of the present invention.

FIG. 14 illustrates a screenshot of a prototype 1000 of the software application according to an embodiment of the present invention. The prototype 1000 is an interactive representation of the application on a virtual platform provided in the graphical user interface. The prototype 1000 enables the developer to use and test the initial version of the application prototype according to the selection of templates and features. The prototype 1000 is generated by a prototype engine 450. The prototype engine 450 generates the prototype based on the integrated build card. Specifically, the prototype engine 450 accepts as an input the set of instantiated features as modified by the integration engine (if edited) and the connections between the features as identified by the integration engine 450 and modified by the user. The prototype engine logically arranges the features of the integrated build card and populates their display and interactive regions according to the edited attributes and rules to provide an operable visual interactive simulation demonstrating a functional prototype of the desired application. The prototype 1000 generated by the prototype engine 450 and transmitted for display by the graphical user interface on the client device is thus a clickable or navigable prototype of the customer's application, in some embodiments. That is, the interface elements of the prototype simulate the operation of the actual application, to the extent possible. For example, a button linked to another feature will bring up that feature when clicked upon or otherwise actuated by the user on the prototype. After operating the prototype, the user may refine the application by returning to the screen flow to edit the integrated build card (add/remove/edit features and their connections) as previously described.

In some embodiments, the build card, the integrated build card, or both, may serve to update the rules database 470. Specifically, the aggregate selections of multiple clients and builds can provide or enhance statistical data on the preferred connections between features as recorded in the rules database. In some embodiments, feature dependencies may be crowdsourced from the historical selections of users of the system. Thus, inter-feature information use in the rules can include the frequency or probability of selecting a specific feature when another is selected. The history may involve many different interactions including inter-screen connections and edits thereof. Other mechanisms for updating the rules database based on the aggregate history of build cards are contemplated.

The editing and selection by the user to adjust or create the described instant prototype can preferably be incorporated into the development process. In particular, the selections may automatically be included in the source code generated for the software application.

Pricing can be integrated using a database in server 430 that contains pricing information and a pricing engine as part of builder application 440 that is configured to determine or identify pricing using the database and as a function of the selected features for an actual software application sought to be developed by the platform.

Server 430 can also have a database in server 430 that contains information about a plurality of software developers including communications address for each and integration into the builder application 440 using communication connection and login credentials. Server 430 can include communication platform using the information from the database to operate a work flow through the various phases using one or more software developers that are integrated into the platform to provide an efficient work flow.

Each of the system, server, computing device, and computer described in this application can be implemented on one or more computer systems and be configured to communicate over a network. In one embodiment, the computer system includes a bus or other communication mechanism for communicating information, and a hardware processor coupled with bus for processing information.

The computer system also includes a main memory, such as a random access memory (RAM) or other dynamic storage device, coupled to bus for storing information and instructions to be executed by a processor of the computer or computing device. Main memory also may be used for storing temporary variables or other intermediate information during execution of instructions to be executed by a processor. Such instructions, when stored in non-transitory storage media accessible to processor, configure the computer system into a special-purpose machine that is customized to perform the operations specified in the instructions and provide or be capable of features and functionality described herein. The processes described herein can be implemented as computer instructions executable by the processor of a computer or computing device to perform described process steps. The computer instructions can be saved on nonvolatile or nontransitory memory for providing such implementations.

The computer system further includes a read only memory (ROM) or other static storage device coupled to bus for storing static information and instructions for processor.

A storage device, such as a magnetic disk or optical disk, is provided and coupled to bus for storing information and instructions.

The computer system may be coupled via bus to a display, such as an LCD, for displaying information to a computer user. An input device, including alphanumeric and other keys, may be coupled to bus for communicating information and command selections to processor. Another type of user input device is cursor control, such as a mouse, a trackball, touchscreen (e.g., on mobile phones) or cursor direction keys for communicating direction information and command selections to processor and for controlling cursor movement on display. This input device typically has two degrees of freedom in two axes, a first axis (e.g., x) and a second axis (e.g., y), that allows the device to specify positions in a plane.

The computer system may implement the techniques described herein using customized hard-wired logic, one or more ASICs or FPGAs, firmware and/or program logic which, in combination with the computer system, causes or programs the computer system to provide specialized features. According to one embodiment, the techniques herein are performed by the computer system in response to the processor executing one or more sequences of one or more instructions contained in main memory. Such instructions may be read into main memory from another storage medium, such as a storage device. Execution of the sequences of instructions contained in main memory causes the processor to perform the process steps described herein. In alternative embodiments, hard-wired circuitry may be used in place of or in combination with software instructions.

The term storage media as used herein refers to any non-transitory media that stores data and/or instructions that cause a machine to operate in a specific fashion. Such storage media may comprise non-volatile media and/or volatile media. Non-volatile media includes, for example, optical or magnetic disks, such as storage device. Volatile media includes dynamic memory, such as main memory. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, or any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus. Transmission media can also take the form of acoustic or light waves, such as those generated during radio-wave and infra-red data communications.

Various forms of media may be involved in carrying one or more sequences of one or more instructions to the processor for execution. For example, the instructions may initially be carried on a magnetic disk or solid state drive of a remote computer. A bus carries the data to the main memory, from which the processor retrieves and executes the instructions. The instructions received by the main memory may optionally be stored on a storage device either before or after execution by the processor.

The computer system also includes a communication interface coupled to bus. The communication interface provides a two-way data communication coupling to a network link that is connected to a local network. For example, the communication interface may be an integrated services digital network (ISDN) card, cable modem, satellite modem, or a modem to provide a data communication connection to a corresponding type of telephone line. As another example, the communication interface may be a local area network (LAN) card to provide a data communication connection to a compatible LAN. Wireless links may also be implemented. In any such implementation, the communication interface sends and receives electrical, electromagnetic or optical signals that carry digital data streams representing various types of information.

Network link typically provides data communication through one or more networks to other data devices. For instance, network link may provide a connection through local network to a host computer or to data equipment operated by an Internet Service Provider (ISP). The ISP in turn provides data communication services through the worldwide packet data communication network now commonly referred to as the "Internet." Local network and Internet both use electrical, electromagnetic or optical signals that carry digital data streams. The signals through the various networks and the signals on the network link and through the communication interface, which carry the digital data to and from the computer system, are example forms of transmission media.

The computer system can send messages and receive data, including program code, through the network(s), network link and the communication interface. In the Internet example, a server might transmit a requested code for an application program through Internet, ISP, local network and the communication interface.

The received code may be executed by the processor as it is received, and/or stored in storage device, or other non-volatile storage for later execution.

It should be understood that variations, clarifications, or modifications are contemplated. Applications of the technology to other fields are also contemplated.

Exemplary systems, devices, components, and methods are described for illustrative purposes. Further, since numerous modifications and changes will readily be apparent to those having ordinary skill in the art, it is not desired to limit the invention to the exact constructions as demonstrated in this disclosure. Accordingly, all suitable modifications and equivalents may be resorted to falling within the scope of the invention.

Thus, for example, any sequence(s) and/or temporal order of steps of various processes or methods that are described herein are illustrative and should not be interpreted as being restrictive. Accordingly, it should be understood that although steps of various processes or methods or connections or sequence of operations may be shown and described as being in a sequence or temporal order, they are not necessarily limited to being carried out in any particular sequence or order. For example, the steps in such processes or methods generally may be carried out in various different sequences and orders, while still falling within the scope of the present invention. Moreover, in some discussions, it would be evident to those of ordinary skill in the art that a subsequent action, process, or feature is in response to an earlier action, process, or feature.

It is also implicit and understood that the applications or systems illustratively described herein provide computer-implemented functionality that automatically performs a process or process steps unless the description explicitly describes user intervention or manual operation.

It is understood from the above description that the functionality and features of the systems, devices, components, or methods of embodiments of the present invention include generating and sending signals to accomplish the actions.

It should be understood that claims that include fewer limitations, broader claims, such as claims without requiring a certain feature or process step in the appended claim or in the specification, clarifications to the claim elements, different combinations, and alternative implementations based on the specification, or different uses, are also contemplated by the embodiments of the present invention.

It should be understood that combinations of described features or steps are contemplated even if they are not described directly together or not in the same context.

The terms or words that are used herein are directed to those of ordinary skill in the art in this field of technology and the meaning of those terms or words will be understood from terminology used in that field or can be reasonably interpreted based on the plain English meaning of the words in conjunction with knowledge in this field of technology. This includes an understanding of implicit features that, for example, may involve multiple possibilities, but to a person of ordinary skill in the art, a reasonable or primary understanding or meaning is understood.

It should be understood that the above-described examples are merely illustrative of some of the many specific examples that represent the principles described herein. Clearly, those skilled in the art can readily devise numerous other arrangements without departing from the scope of the present invention.

What is claimed is:

1. An online software development system for developing software applications, comprising:
    at least one processor; and
    at least one memory operatively coupled to the at least one processor, the at least one processor configured to acquire computer readable instructions stored in the at least one memory and execute the instructions comprising instructions to cause the online software development system to:
        receive a plurality of wireframes prepared for a proposed custom software application sought to be developed by a user of the online software development system;
        perform a comparison between the wireframes and software screens for previously developed custom software applications;
        detect matches between the wireframes and software screens;
        identify features available on the online software development system for developing custom software applications that correspond to the matches;
        provide a graphical user interface on a display of a client device, and implement simulations of a plurality of features available for demonstration through the graphical user interface;
        store blocks of source code for each feature in a source code repository, wherein the blocks are adapted to provide an actual application when compiled by developers;
        receive from the client device, by a server running a software building component of a software development application, one or more selected features for the proposed custom software application;
        automatically integrate, by the software building component, the one or more selected features to generate an integrated feature set based on attributes of each of the selected features and an inter-feature rules set, and
        generate on the graphical user interface an interactive visualization of a navigable prototype of the software application based on the integrated feature set.

2. The online software development system of claim 1 wherein the computer readable instructions further cause the processor to generate a specification that identifies components of software to be developed to complete the proposed custom software application.

3. The online software development system of claim 1, wherein the comparison comprises comparison of images of wireframes with images of software screens previously developed for available features on the online software development system.

4. The online software development system of claim 3, wherein the systems comprises a plurality of use-selectable features that are automatically detected from the wireframes to be included in the proposed customer software application.

5. The online software development system of claim 1, wherein the instructions further comprise instructions to cause the processor to provide a normalization engine that operates on the wireframes.

6. The online software development system of claim 1, wherein the instructions further comprise instructions to cause the processor to generate images of developed software screens and store an association of the images to corresponding features.

7. The online software development system of claim 6, wherein the instructions further comprise instructions to cause the provide a normalization engine that operates on the generated images of developed software screens.

8. The online software development system of claim 1, wherein the instructions further comprise instructions to cause the process to generate digital rules or parameters that translate image content of wireframe screens to available features on the software development system.

9. A computer-implemented method for online software development of custom software applications, comprising:
    receiving a plurality of wireframes prepared for a proposed custom software application sought to be developed by a user;
    performing a comparison between the wireframes and software screens for previously developed custom software applications;
    detecting matches between the wireframes and software screens;
    identifying features available on an online software development application for developing custom software applications that correspond to the matches;
    providing a graphical user interface on a display of a client device, and implement simulations of a plurality of features available for demonstration through the graphical user interface;
    storing blocks of source code for each feature in a source code repository, wherein the blocks are adapted to provide an actual application when compiled by developers;
    receiving from the client device, by a server running a software building component of the online software development application, one or more selected features for the proposed custom software application;
    automatically integrating, by the software building component, the one or more selected features to generate an integrated feature set based on attributes of each of the selected features and an inter-feature rules set, and generating on the graphical user interface an interactive visualization of a navigable prototype of the software application based on the integrated feature set.

10. The computer-implemented method of claim 9 further comprising identifying components of software to be developed to complete the proposed custom software application.

11. The computer-implemented method of claim 9, wherein the comparison comprises comparison of images of wireframes with images of software screens previously developed for available features on the online software development system.

12. The computer-implemented method of claim 11, comprising providing a plurality of use-selectable features that are automatically detected from the wireframes to be included in the proposed customer software application.

13. The computer-implemented method of claim 9, further comprising applying a normalization engine that operates on the wireframes.

14. The computer-implemented method of claim 9, further comprising generating images of developed software screens and store an association of the images to corresponding features.

15. The computer-implemented method of claim 14, further comprising implementing a normalization engine that operates on the generated images of developed software screens.

16. The computer-implemented method of claim 9, further comprising generating digital rules or parameters that translate image content of wireframe screens to available features on the software development system.

17. Computer readable medium, comprising nonvolatile memory, wherein the nonvolatile memory comprising computer readable instructions that are executed by a computer and configure the computer to operate, where in the computer readable instructions comprising steps including:

receiving a plurality of wireframes prepared for a proposed custom software application sought to be developed by a user of a online software development system;

performing a comparison between the wireframes and software screens for previously developed custom software applications;

detecting matches between the wireframes and software screens;

identifying features available on the online software development system for developing custom software applications that correspond to the matches;

providing a graphical user interface on a display of a client device, and implement simulations of a plurality of features available for demonstration through the graphical user interface;

storing blocks of source code for each feature in a source code repository, wherein the blocks are adapted to provide an actual application when compiled by developers;

receiving from the client device, by a server running a software building component of a software development application, one or more selected features for the proposed custom software application;

automatically integrating, by the software building component, the one or more selected features to generate an integrated feature set based on attributes of each of the selected features and an inter-feature rules set, and generating on the graphical user interface an interactive visualization of a navigable prototype of the software application based on the integrated feature set.

18. The computer readable medium of claim 17, wherein the computer readable instructions further cause the computer to generate a specification that identifies components of software to be developed to complete the proposed custom software application.

19. The computer readable medium of claim 17, wherein the computer readable instructions cause the computer to generate images of developed software screens and store an association of the images to corresponding features.

20. The computer readable medium of claim 17, wherein the computer readable instructions cause the computer to generate digital rules or parameters that translate image content of wireframe screens to available features on the software development system.

* * * * *